(12) United States Patent
Claes et al.

(10) Patent No.: US 8,741,608 B2
(45) Date of Patent: Jun. 3, 2014

(54) PROCESS FOR THE FERMENTATIVE PREPARATION OF L-ORNITHINE

(75) Inventors: Wilfried Claes, Bielefeld (DE); Robert Gerstmeir, Werther (DE)

(73) Assignee: Evonik Degussa GmbH, Essen (DE)

( * ) Notice: Subject to any disclaimer, the term of this patent is extended or adjusted under 35 U.S.C. 154(b) by 244 days.

(21) Appl. No.: 13/074,458

(22) Filed: Mar. 29, 2011

(65) Prior Publication Data

US 2011/0244529 A1    Oct. 6, 2011

(30) Foreign Application Priority Data

Mar. 30, 2010    (DE) .......................... 10 2010 003 419

(51) Int. Cl.
    *C12P 13/10*    (2006.01)
(52) U.S. Cl.
    USPC ........................................................... 435/114
(58) Field of Classification Search
    USPC ........................................................... 435/114
    See application file for complete search history.

(56) References Cited

U.S. PATENT DOCUMENTS

2003/0124687 A1    7/2003    Gunji et al.
2008/0199919 A1    8/2008    Gunji et al.

FOREIGN PATENT DOCUMENTS

EP    1 266 966 A2    12/2002
EP    1 266 966 A3    12/2002

OTHER PUBLICATIONS

International Search Report issued Nov. 24, 2011 in Application No. PCT/EP2011/054541 (With English Translation of Category of Cited Documents).
A. Bellmann, et al., "Expression control and specificity of the basic amino acid exporter LysE of Corynebacterium glutamicum", Microbiology, vol. 147, No. 7, 2001, pp. 1765-1774.
Yoshiya Gunji, et al., "Enhancement of L-lysine production in methylotroph Methylophilus methylotrophus by introducing a mutant LysE exporter", Journal of Biotechnology, vol. 127, No. 1, 2006, pp. 1-13.
Marina Vrljic, et al., "A new type of transporter with a new type of cellular function: L-lysine export from Corynebacterium glutamicum", Molecular Microbiology, vol. 22, No. 5, 1996, pp. 815-826.

*Primary Examiner* — Tekchand Saidha
(74) *Attorney, Agent, or Firm* — Oblon, Spivak, McClelland, Maier & Neustadt, L.L.P.

(57) ABSTRACT

A process for the fermentative preparation of L-ornithine using microorganisms characterized by an increased export of the amino acid.

14 Claims, 3 Drawing Sheets

Fig. 1A

Alignment of the amino acid sequences of the LysE and ArgO proteins listed in Table 1. Alignment gaps are indicated by "-". Identical amino acids are indicated by "*".

```
YP_225551.1       ------------------MEIFITGLLLGASLLLSIGPQNVLVIKQGIKREGLIAVLLV
ZP_05749209.1     ------------------MEIFVTGLLLGASLLLAIGPQNVLVIKQGIKREGITAVIIV
NP_939452.1       ------------------MSIAIAGFLMGLSLIVAIGPQNALIIRQGIKREGLIPILVV
ZP_03933958.1     ------------------MSVLLAGFLLGLSLIVAIGPQNAYIIKMGVKRDHIGAIILA
YP_002834652.1    MRRLEA------------MSVLLAGFALGLSLIIAIGPQNAYIIKMGIKRDHVGPILLA
ZP_03711883.1     ------------------MSIAVAGFLLGLSLIVAIGPQNALVIRQGVKREGLIVVLAI
ZP_03922319.1     ------------------MSIVLAGFFLGLSLIVAVGPQNAMLLKYGIRRDHIGLIIVV
ZP_03931790.1     ------------------MSIVLAGFVLGLSLIVAVGPQNAMLLKYGIRRDHIGLIIVV
ZP_03918361.1     MVPENLSFYLCVLLTHNKYVNVFFAGLLFNLSLILALGPQNALILKYGLRRQAITLVISV
YP_002958101.1    M-----------------WTLAGTGLLTGLALIVAIGAQNAFVLRQGVRREHVGAVVLV
ZP_05365683.1     ------------------MSIVLAGFFLGLSLIVAVGPQNAMLLKYGIRRDHIGLIIVV
ZP_04835056.1     ------------------MSIAVAGFLLGLSLIVAIGPQNALVIRQGVKREGLIVVLAI
                                    *     *   * **       *   *

YP_225551.1       CLISDVFLFIAGTLGVDLLSNAAPIVLDIMRWGGIAYLLWFAVMAAKDAMTNKVEA----
ZP_05749209.1     CLLSDVVLFTLGTLGVGLISDTAPIILDILRWCGIAYLLWFAVMAARDALRARTEV----
NP_939452.1       CILSDVILIFGGTAGVGALVDRAPIALVVLKWLGVAYLLYFGFTCFKEAFKRHGQA----
ZP_03933958.1     CLLSDVILINAGVGGMGVLVEKFPTGLIIMKYLGAAYLIYFGFTCFRDAFKKEQEA----
YP_002834652.1    CLLSDVILITGGTAGVGVLVERFPTALVVVKYLGAAYLIYFGFTCFRDAFKKQQDA----
ZP_03711883.1     CILSDIFLIFGGTAGVGVIIEKAPLALVALKWFGAAYLAWFAVSCFRDMV--KPRA----
ZP_03922319.1     CALSDVILITSGTAGVGYLVEKFPNALQVLKYVGAAYLAYFTFTCFRDAFKTKGEA----
ZP_03931790.1     CALSDVILITSGTAGVGYLVERFPNALEALKYIGAAYLAFFTFTCFRDAFKTKGEAIDVE
ZP_03918361.1     CALCDITLIALSGVGVGVILQKAPIVLRIYAGFLYLLWFAYTCFRDAIHPKTLA----
YP_002958101.1    CMASDAVLILAGTAGVGALVQAVPWLLEVLRWGGALYLLWFAVSSLRAAL-----R----
ZP_05365683.1     CALSDVILITSGTAGVGYLVEKFPNALQVLKYVGAAYLAYFTFTCFRDALKTKGEA----
ZP_04835056.1     CMLSDIFLIFGGTAGVGVIIEKAPLALVALKWFGAAYLAWFAVSCFKDMVKPRALD----
                   *   *  *       *       *   *    * *   *  * **  *

YP_225551.1       ---PQ-IIE-----ETEP---T--VP-----D-DTP-LG----------G-----SAVAT
ZP_05749209.1     ---T--FVE-----HSEP---V--AA-----A-SAS-GG----------G---------V
NP_939452.1       ----L-AVE-----QSEP---V--AY-----E-PVA-DA----------S-----SGVIT
ZP_03933958.1     ----L-VVS-----STPP---S--AP-----N-ETE-LG----------G------ATTV
YP_002834652.1    ----L-VIE-----ETTP---VAQVV-----D-ENS-GN----------A-----GAPGT
ZP_03711883.1     ---LD-SSA-----TDDG---T--SL-----D-DAP-TAAHVSNVDTTSG-----NGGQV
ZP_03922319.1     ---IE-V-E-----STQP---K--AP-----Q-EVASFD----------G-----SQARS
ZP_03931790.1     STSPN-STE-----EVAT---F--DG-----D-GDS-TG----------GVGTEHGSVAT
ZP_03918361.1     ---TE-TVS-----ETKPHEEE--LP-----DVSST-TA----------G-----TTMAT
YP_002958101.1    ---PQGLMA-----EQAP---R--T-----------A----------G-----SVIAT
ZP_05365683.1     ---IE-V-E-----STQP---K--VP-----Q-EVASFD----------G-----SQARN
ZP_04835056.1     ---SS-ATDNGTSLDDAP---T--VAHISNVD-STS-GN----------G-----GQVQT

YP_225551.1       DTRNRVRVEVS--VDKQ----RVWVK------PMLMAIVLTWLNPNAYLDAFVFIGGVG
ZP_05749209.1     TTKQRPRLRIT--SGTR----QVWVR------PMLMAIVLTWLNPNAYLDAFVFIGGVG
NP_939452.1       KTRTKAQPK-----SAQ----RTWVK------PVLAALAFTWLNPAAYIDVLVMLGGIA
ZP_03933958.1     MTKQRT--------KS-----RTWVK------PVMGAMALTWLNPLAYVDVLVMLGGIA
YP_002834652.1    SVLTKIRPRV----RS-----KSWVK------PVLGALALTWLNPLAYVDALVMLGGIA
ZP_03711883.1     QTKTRPITTTA--PTRQAHPARPWVK------PALAALAFTWLNPSAYIDTLVMLGGIA
ZP_03922319.1     TTKTAARVEIK---RS-----PSWVK------PLLTALALTWLNPGAYVDVVVMLGSIA
ZP_03931790.1     ATATQ-RQEIK---RS-----PSWVK------PLLTALALTWLNPGAYVDVLVMLGGIA
ZP_03918361.1     ATVMETATTVK--EKTH----RRTFHIPQEIKGPAVAAFVVSVINPAAWVDLFVVIGSIS
YP_002958101.1    ------------------------------TLALTWLNPHVYLDTVVLLGSLA
```

To Fig. 1B

From Fig. 1A

Fig. 1B

```
ZP_05365683.1      TTKTATRVEIK----RS----PSWVK-------PLLTALALTWLNPGAYVDVVVMLGSIA
ZP_04835056.1      KTRPITTTAPTRQAHPA----RPWVK-------PALAALAFTWLNPSAYIDTLVMLGGIA
                                                     **    *   *   *

YP_225551.1        AQYGDTGRWIFAAGAFAASLIWFPLVGFGAAALSRPLSSPKVWRWINVVVAVVMTALAIK
ZP_05749209.1      AQYGETGRWIFAAGAFAASLVWFPLVGYGAAALSRPLSSPRVWRWINIGVAVVLTGLAVK
NP_939452.1        NQHGPDGRWVFALGALCASLTWFPFIGYTSTRFSTVLSRPAVWRYINIAIGIIMMIMCAR
ZP_03933958.1      QHYGDQ-RWVFAAGAIMASAVWFPTVGYGAFKLSHVLAKPTTWRYVNFAICCVMMLLTAK
YP_002834652.1     NQYGDQ-RWVFAGGAILASAVWFPSLGFGAYKLSHVLAKPTTWRVVNIVIGCVMLALTAK
ZP_03711883.1      NQHGESGRWVFAAGALMASAVWFPLLGFFSTRFSRVLSRPQAWRVINGVIGCIMVVMCIR
ZP_03922319.1      NQYGESGRWLFAVGAICASFTWFPFIGFCAARFSHVLSRPTVWRWINFGIGVIMIGLTLK
ZP_03931790.1      NQYGDPGRWLFAGGAIAASFTWFPVIGFGAARFSHVLSRPEVWRWINVGIGVIMIGLTLK
ZP_03918361.1      SSYGP-DKWAFLLGTMAASLVWFPAFGYGAAALSRPLSSPKVWRCINTGIGLFMVFMAFR
YP_002958101.1     NQHGPDARWVFAAGAVAASVLWFTALGYGARLLARVLADPKAWRVVDVVIAVVMAVLAVR
ZP_05365683.1      NQYGESGRWLFAVGAICASFTWFPFIGFCAARFSHVLSRPTVWRWINFGIGVIMIGLTLK
ZP_04835056.1      NQHGESGRWVFAAGALMASAVWFPLLGFFSTRFSRVLSRPQAWRVINGVIGCIMVVMCIR
                      *    *   *    **  **   *              *   * **

YP_225551.1        LMLMG----
ZP_05749209.1      LILMG----
NP_939452.1        LIMH-----
ZP_03933958.1      LLLH-----
YP_002834652.1     LLFL-----
ZP_03711883.1      LVMH-----
ZP_03922319.1      LLLL-----
ZP_03931790.1      LLLL-----
ZP_03918361.1      VLFM-----
YP_002958101.1     LIAGSDVWG
ZP_05365683.1      LLLL-----
ZP_04835056.1      LIMH-----
```

Setting of the Clone Manager 9 program from Scientific and
Educational Software for determining the identity of two
amino acid sequences by global sequence alignment.

SEQUENCE LISTING

```
<160> NUMBER OF SEQ ID NOS: 30

<210> SEQ ID NO 1
<211> LENGTH: 1901
<212> TYPE: DNA
<213> ORGANISM: Corynebacterium glutamicum ATCC13032
<220> FEATURE:
<221> NAME/KEY: misc_feature
<222> LOCATION: (930)..(61)
<223> OTHER INFORMATION: Complementary Strand of Coding region of
      Regulator lysG coding for ACtivator protein LysG
<220> FEATURE:
<221> NAME/KEY: misc_feature
```

```
<222> LOCATION: (1000)..(1000)
<223> OTHER INFORMATION: Transcription start of lysE-Gens
<220> FEATURE:
<221> NAME/KEY: CDS
<222> LOCATION: (1001)..(1702)
<223> OTHER INFORMATION: Coding region of lysE-Gens

<400> SEQUENCE: 1
```

| | | |
|---|---|---:|
| cctggcccaa ttcctgcggg cgaagaagtg aaaaaccctg aacctttca gaagtaacta | | 60 |
| aggccgcaat ccctcgattg ctgcatcaac gacggcgtct gtgagtctag ctagagatct | | 120 |
| agattccagg cgccatcgtt gccaatacat cggtgtgtca atgggtatct catcgaggag | | 180 |
| gatcacttct cctgctttta gcatgggagc agcttgggtt tcgggaagaa gtccccaacc | | 240 |
| aaggcctcgg cgaattgcct caccaaaaacc ttccgccgac gggacaatgg atacgcgcct | | 300 |
| gcgccccaca ggaccatcga cgcgcccgtc caggtcacgg tcttgaagca catctttggg | | 360 |
| accgaagcgt aagacgggca tcgcagccca atctagtttc ccatcaacca tgtaggcatc | | 420 |
| ccgcaatgag ggggttgcaa tggccaagtg gcgcatggtt ccaagttcta ctacttcaca | | 480 |
| tcccgccacg ggattagctt cacgggttac cgctcctaaa acatctccac gccgcagcaa | | 540 |
| ggataatgtg tgcgcttcat cttccaagcg cagcgtgagc gttgctccac cccaagaagc | | 600 |
| tacctcgttg aacacgggag gaaaccatgt ggatagcgaa tctgcgttga tggcgatggt | | 660 |
| taacgggatt tcagcaaggc gtccagatag ttgcgcttta gtttctgctt gcagcaacac | | 720 |
| cattttccgc gctgcttgca caaggacttc acccgcttcg gttgctttgg ccggttgggt | | 780 |
| gcgcgatacc aacactcgac ccacgtgatg ctcgagagct ttaacgcgct gactcaccgc | | 840 |
| cgaggggaa atggaaaggg ctaaggaggc gccttcgaag ctgccttcat caatgattga | | 900 |
| gagcaaagtg tccagttgaa tggggttcat gaagctatat taaaccatgt taagaaccaa | | 960 |
| tcattttact taagtacttc cataggtcac gatggtgatc atg gaa atc ttc att | | 1015 |
| | Met Glu Ile Phe Ile | |
| | 1        5 | |
| aca ggt ctg ctt ttg ggg gcc agt ctt tta ctg tcc atc gga ccg cag | | 1063 |
| Thr Gly Leu Leu Leu Gly Ala Ser Leu Leu Leu Ser Ile Gly Pro Gln | | |
|     10              15                  20 | | |
| aat gta ctg gtg att aaa caa gga att aag cgc gaa gga ctc att gcg | | 1111 |
| Asn Val Leu Val Ile Lys Gln Gly Ile Lys Arg Glu Gly Leu Ile Ala | | |
|         25              30              35 | | |
| gtt ctt ctc gtg tgt tta att tct gac gtc ttt ttg ttc atc gcc ggc | | 1159 |
| Val Leu Leu Val Cys Leu Ile Ser Asp Val Phe Leu Phe Ile Ala Gly | | |
|     40              45                  50 | | |
| acc ttg ggc gtt gat ctt ttg tcc aat gcc gcg ccg atc gtg ctc gat | | 1207 |
| Thr Leu Gly Val Asp Leu Leu Ser Asn Ala Ala Pro Ile Val Leu Asp | | |
|     55              60              65 | | |
| att atg cgc tgg ggt ggc atc gct tac ctg tta tgg ttt gcc gtc atg | | 1255 |
| Ile Met Arg Trp Gly Gly Ile Ala Tyr Leu Leu Trp Phe Ala Val Met | | |
| 70          75              80              85 | | |
| gca gcg aaa gac gcc atg aca aac aag gtg gaa gcg cca cag atc att | | 1303 |
| Ala Ala Lys Asp Ala Met Thr Asn Lys Val Glu Ala Pro Gln Ile Ile | | |
|             90              95              100 | | |
| gaa gaa aca gaa cca acc gtg ccc gat gac acg cct ttg ggc ggt tcg | | 1351 |
| Glu Glu Thr Glu Pro Thr Val Pro Asp Asp Thr Pro Leu Gly Gly Ser | | |
|             105             110             115 | | |
| gcg gtg gcc act gac acg cgc aac cgg gtg cgg gtg gag gtg agc gtc | | 1399 |
| Ala Val Ala Thr Asp Thr Arg Asn Arg Val Arg Val Glu Val Ser Val | | |
|         120             125             130 | | |
| gat aag cag cgg gtt tgg gta aag ccc atg ttg atg gca atc gtg ctg | | 1447 |
| Asp Lys Gln Arg Val Trp Val Lys Pro Met Leu Met Ala Ile Val Leu | | |
|     135             140             145 | | |

```
acc tgg ttg aac ccg aat gcg tat ttg gac gcg ttt gtg ttt atc ggc      1495
Thr Trp Leu Asn Pro Asn Ala Tyr Leu Asp Ala Phe Val Phe Ile Gly
150                 155                 160                 165 ggc gtc ggc gcg caa tac ggc gac acc gga cgg tgg att ttc gcc gct      1543
Gly Val Gly Ala Gln Tyr Gly Asp Thr Gly Arg Trp Ile Phe Ala Ala
            170                 175                 180 ggc gcg ttc gcg gca agc ctg atc tgg ttc ccg ctg gtg ggt ttc ggc      1591
Gly Ala Phe Ala Ala Ser Leu Ile Trp Phe Pro Leu Val Gly Phe Gly
        185                 190                 195 gca gca gca ttg tca cgc ccg ctg tcc agc ccc aag gtg tgg cgc tgg      1639
Ala Ala Ala Leu Ser Arg Pro Leu Ser Ser Pro Lys Val Trp Arg Trp
    200                 205                 210 atc aac gtc gtc gtg gca gtt gtg atg acc gca ttg gcc atc aaa ctg      1687
Ile Asn Val Val Val Ala Val Val Met Thr Ala Leu Ala Ile Lys Leu
215                 220                 225 atg ttg atg ggt tag ttttcgcggg ttttggaatc ggtggccttc gcccaaatgt      1742
Met Leu Met Gly
230 tgatgccggc gtcgtgggaa atctcatcga tcgcctccaa ctcggcgtca gaaaactcca   1802 agttgttgag tgaatcaagg ctgttgtcca gctgctcaac tgacgaagca ccaatcaatg   1862 cactggtcac ggtatccgcg ccgtactctc cttgctcgc                          1901

<210> SEQ ID NO 2
<211> LENGTH: 233
<212> TYPE: PRT
<213> ORGANISM: Corynebacterium glutamicum ATCC13032

<400> SEQUENCE: 2

Met Glu Ile Phe Ile Thr Gly Leu Leu Leu Gly Ala Ser Leu Leu Leu
1               5                   10                  15

Ser Ile Gly Pro Gln Asn Val Leu Val Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
    50                  55                  60

Pro Ile Val Leu Asp Ile Met Arg Trp Gly Gly Ile Ala Tyr Leu Leu
65                  70                  75                  80

Trp Phe Ala Val Met Ala Ala Lys Asp Ala Met Thr Asn Lys Val Glu
                85                  90                  95

Ala Pro Gln Ile Ile Glu Glu Thr Glu Pro Thr Val Pro Asp Asp Thr
            100                 105                 110

Pro Leu Gly Gly Ser Ala Val Ala Thr Asp Thr Arg Asn Arg Val Arg
        115                 120                 125

Val Glu Val Ser Val Asp Lys Gln Arg Val Trp Val Lys Pro Met Leu
    130                 135                 140

Met Ala Ile Val Leu Thr Trp Leu Asn Pro Asn Ala Tyr Leu Asp Ala
145                 150                 155                 160

Phe Val Phe Ile Gly Gly Val Gly Ala Gln Tyr Gly Asp Thr Gly Arg
                165                 170                 175

Trp Ile Phe Ala Ala Gly Ala Phe Ala Ala Ser Leu Ile Trp Phe Pro
            180                 185                 190

Leu Val Gly Phe Gly Ala Ala Ala Leu Ser Arg Pro Leu Ser Ser Pro
        195                 200                 205

Lys Val Trp Arg Trp Ile Asn Val Val Val Ala Val Val Met Thr Ala
    210                 215                 220
```

```
Leu Ala Ile Lys Leu Met Leu Met Gly
225                 230
```

<210> SEQ ID NO 3
<211> LENGTH: 761
<212> TYPE: DNA
<213> ORGANISM: Corynebacterium glutamicum ATCC13032
<220> FEATURE:
<221> NAME/KEY: PCR-lysE-Fragment
<222> LOCATION: (1)..(761)

<400> SEQUENCE: 3

```
tcgatatcat ggaaatcttc attacaggtc tgcttttggg ggccagtctt ttactgtcca    60
tcggaccgca gaatgtactg gtgattaaac aaggaattaa gcgcgaagga ctcattgcgg   120
ttcttctcgt gtgtttaatt tctgacgtct ttttgttcat cgccggcacc ttgggcgttg   180
atcttttgtc caatgccgcg ccgatcgtgc tcgatattat gcgctggggt ggcatcgctt   240
acctgttatg gtttgccgtc atggcagcga agacgccat gacaaacaag gtggaagcgc   300
cacagatcat tgaagaaaca gaaccaaccg tgcccgatga cacgcctttg gcggttcgg   360
cggtggccac tgacacgcgc aaccgggtgc gggtggaggt gagcgtcgat aagcagcggg   420
tttgggtaaa gcccatgttg atggcaatcg tgctgacctg gttgaacccg aatgcgtatt   480
tggacgcgtt tgtgtttatc ggcggcgtcg gcgcgcaata cggcgacacc ggacggtgga   540
ttttcgccgc tggcgcgttc gcggcaagcc tgatctggtt cccgctggtg ggtttcggcg   600
cagcagcatt gtcacgcccg ctgtccagcc caaggtgtg gcgctggatc aacgtcgtcg   660
tggcagttgt gatgaccgca ttggccatca aactgatgtt gatgggttag ttttcgcggg   720
ttttggaatc ggtggccttc gcccaaatat tgacctaggc a                       761
```

<210> SEQ ID NO 4
<211> LENGTH: 236
<212> TYPE: PRT
<213> ORGANISM: Corynebacterium glutamicum R
<220> FEATURE:
<221> NAME/KEY: LysE
<222> LOCATION: (1)..(236)

<400> SEQUENCE: 4

```
Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
        115                 120                 125

Arg Val Arg Val Glu Val Ser Val Asp Lys Gln Arg Val Trp Val Lys
    130                 135                 140

Pro Met Leu Met Ala Ile Val Leu Thr Trp Leu Asn Pro Asn Ala Tyr
```

```
              145                 150                 155                 160
Leu Asp Ala Phe Val Phe Ile Gly Gly Val Gly Ala Gln Tyr Gly Asp
                    165                 170                 175

Thr Gly Arg Trp Ile Phe Ala Ala Gly Ala Phe Ala Ala Ser Leu Ile
                180                 185                 190

Trp Phe Pro Leu Val Gly Phe Gly Ala Ala Ala Leu Ser Arg Pro Leu
            195                 200                 205

Ser Ser Pro Lys Val Trp Arg Trp Ile Asn Val Val Ala Val Val
        210                 215                 220

Met Thr Ala Leu Ala Ile Lys Leu Met Leu Met Gly
225                 230                 235

<210> SEQ ID NO 5
<211> LENGTH: 233
<212> TYPE: PRT
<213> ORGANISM: Corynebacterium glutamicum ATCC14067
<220> FEATURE:
<221> NAME/KEY: LysE
<222> LOCATION: (1)..(233)

<400> SEQUENCE: 5

Met Glu Ile Phe Ile Thr Gly Leu Leu Leu Gly Ala Ser Leu Leu Leu
1               5                   10                  15

Ser Ile Gly Pro Gln Asn Val Leu Val Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
    50                  55                  60

Pro Ile Val Leu Asp Ile Met Arg Trp Gly Gly Ile Ala Tyr Leu Leu
65                  70                  75                  80

Trp Phe Ala Val Met Ala Ala Lys Asp Ala Met Thr Asn Lys Val Glu
                85                  90                  95

Ala Pro Gln Ile Ile Glu Glu Thr Glu Pro Thr Val Pro Asp Asp Thr
            100                 105                 110

Pro Leu Gly Gly Ser Ala Val Ala Thr Asp Thr Arg Asn Arg Val Arg
        115                 120                 125

Val Glu Val Ser Val Asp Lys Gln Arg Val Trp Val Lys Pro Met Leu
    130                 135                 140

Met Ala Ile Val Leu Thr Trp Leu Asn Pro Asn Ala Tyr Leu Asp Ala
145                 150                 155                 160

Phe Val Phe Ile Gly Gly Val Gly Ala Gln Tyr Gly Asp Thr Gly Arg
                165                 170                 175

Trp Ile Phe Ala Ala Gly Ala Phe Ala Ala Ser Leu Ile Trp Phe Pro
            180                 185                 190

Leu Val Gly Phe Gly Ala Ala Ala Leu Ser Arg Pro Leu Ser Ser Pro
        195                 200                 205

Lys Val Trp Arg Trp Ile Asn Val Val Ala Val Val Met Thr Ala
    210                 215                 220

Leu Ala Ile Lys Leu Met Leu Met Gly
225                 230

<210> SEQ ID NO 6
<211> LENGTH: 702
<212> TYPE: DNA
<213> ORGANISM: Corynebacterium glutamicum ATCC14067
<220> FEATURE:
<221> NAME/KEY: lysE-CDS
```

<222> LOCATION: (1)..(702)

<400> SEQUENCE: 6

```
atggaaatct tcattacagg tctgcttttg ggggccagtc ttttgctgtc catcggaccg      60
cagaatgtac tggtgattaa acaaggaatt aagcgcgaag gactcattgc ggttcttctc     120
gtgtgtttaa ttctgacgt cttttgttc atcgccggca ccttgggcgt tgatcttttg      180
tccaatgccg cgccgatcgt gctcgatatt atgcgctggg gtggtatcgc ttacctgtta    240
tggtttgccg tcatggcagc gaaagacgcc atgacaaaca aggtggaagc gccacagatc    300
attgaagaaa cagaaccaac cgtgcccgat gacacgcctt gggcggttc ggcggtggcc      360
actgacacgc gcaaccgggt gcgggtggag gtgagcgtcg ataagcagcg ggtttgggta    420
aagcccatgt tgatgcaat cgtgctgacc tggttgaacc cgaatgcgta tttggacgcg     480
tttgtgttta tcggcggcgt cggcgcgcaa tacggcgaca ccggacggtg gattttcgcc    540
gctggcgcgt tcgcggcaag cctgatctgg ttcccgctgg tgggtttcgg cgcagcagca    600
ttgtcacgcc cgctgtccag ccccaaggtg tggcgctgga tcaacgtcgt cgtggcagtt    660
gtgatgaccg cattggccat caaactgatg ttgatgggtt ag                       702
```

<210> SEQ ID NO 7
<211> LENGTH: 233
<212> TYPE: PRT
<213> ORGANISM: Corynebacterium glutamicum ATCC13869
<220> FEATURE:
<221> NAME/KEY: LysE
<222> LOCATION: (1)..(233)

<400> SEQUENCE: 7

```
Met Glu Ile Phe Ile Thr Gly Leu Leu Leu Gly Ala Ser Leu Leu Leu
1               5                   10                  15

Ser Ile Gly Pro Gln Asn Val Leu Val Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
    50                  55                  60

Pro Ile Val Leu Asp Ile Met Arg Trp Gly Gly Ile Ala Tyr Leu Leu
65                  70                  75                  80

Trp Phe Ala Val Met Ala Ala Lys Asp Ala Met Thr Asn Lys Val Glu
                85                  90                  95

Ala Pro Gln Ile Ile Glu Glu Thr Glu Pro Thr Val Pro Asp Asp Thr
            100                 105                 110

Pro Leu Gly Gly Ser Ala Val Ala Thr Asp Thr Arg Asn Arg Val Arg
        115                 120                 125

Val Glu Val Ser Val Asp Lys Gln Arg Val Trp Val Lys Pro Met Leu
    130                 135                 140

Met Ala Ile Val Leu Thr Trp Leu Asn Pro Asn Ala Tyr Leu Asp Ala
145                 150                 155                 160

Phe Val Phe Ile Gly Gly Val Gly Ala Gln Tyr Gly Asp Thr Gly Arg
                165                 170                 175

Trp Ile Phe Ala Ala Gly Ala Phe Ala Ala Ser Leu Ile Trp Phe Pro
            180                 185                 190

Leu Val Gly Phe Gly Ala Ala Ala Leu Ser Arg Pro Leu Ser Ser Pro
        195                 200                 205

Lys Val Trp Arg Trp Ile Asn Val Val Val Ala Val Val Met Thr Ala
    210                 215                 220
```

```
Leu Ala Ile Lys Leu Met Leu Met Gly
225                 230
```

<210> SEQ ID NO 8
<211> LENGTH: 702
<212> TYPE: DNA
<213> ORGANISM: Corynebacterium glutamicum ATCC13869
<220> FEATURE:
<221> NAME/KEY: lysE-CDS
<222> LOCATION: (1)..(702)

<400> SEQUENCE: 8

```
atggaaatct tcattacagg tctgcttttg ggggccagtc ttttgctgtc catcggaccg    60
cagaatgtac tggtgattaa acaaggaatt aagcgcgaag gactcattgc ggttcttctc   120
gtgtgtttaa tttctgacgt cttttttgttc atcgccggca ccttgggcgt tgatcttttg   180
tccaatgccg cgccgatcgt gctcgatatt atgcgctggg gtggcatcgc ttacctgtta   240
tggtttgccg tcatggcagc gaaagacgcc atgacaaaca aggtggaagc gccacagatc   300
attgaagaaa cagaaccaac cgtgcccgat gacacgcctt gggcggttc ggcggtggcc    360
actgacacgc gcaaccgggt gcgggtggag gtgagcgtcg ataagcagcg ggtttgggtg   420
aagcccatgt tgatggcaat cgtgctgacc tggttgaacc cgaatgcgta tttggacgcg   480
tttgtgttta tcggcggcgt cggcgcgcaa tacggcgaca ccggacggtg gattttcgcc   540
gctggcgcgt tcgcggcaag cctgatctgg ttcccgctgg tgggtttcgg cgcagcagca   600
ttgtcacgcc cgctgtccag ccccaaggtg tggcgctgga tcaacgtcgt cgtggcagtt   660
gtgatgaccg cattggccat caaactgatg ttgatgggtt ag                      702
```

<210> SEQ ID NO 9
<211> LENGTH: 228
<212> TYPE: PRT
<213> ORGANISM: Corynebacterium efficiens YS-314
<220> FEATURE:
<221> NAME/KEY: LysE
<222> LOCATION: (1)..(228)

<400> SEQUENCE: 9

```
Met Glu Ile Phe Val Thr Gly Leu Leu Leu Gly Ala Ser Leu Leu Leu
1               5                   10                  15

Ala Ile Gly Pro Gln Asn Val Leu Val Ile Lys Gln Gly Ile Lys Arg
            20                  25                  30

Glu Gly Ile Thr Ala Val Ile Ile Val Cys Leu Leu Ser Asp Val Val
        35                  40                  45

Leu Phe Thr Leu Gly Thr Leu Gly Val Gly Leu Ile Ser Asp Thr Ala
    50                  55                  60

Pro Ile Ile Leu Asp Ile Leu Arg Trp Cys Gly Ile Ala Tyr Leu Leu
65                  70                  75                  80

Trp Phe Ala Val Met Ala Ala Arg Asp Ala Leu Arg Ala Arg Thr Glu
                85                  90                  95

Val Thr Phe Val Glu His Ser Glu Pro Val Ala Ala Ala Ser Ala Ser
            100                 105                 110

Gly Gly Gly Val Thr Thr Lys Gln Arg Pro Arg Leu Arg Ile Thr Ser
        115                 120                 125

Gly Thr Arg Gln Val Trp Val Arg Pro Met Leu Met Ala Ile Val Leu
    130                 135                 140

Thr Trp Leu Asn Pro Asn Ala Tyr Leu Asp Ala Phe Val Phe Ile Gly
145                 150                 155                 160
```

```
Gly Val Gly Ala Gln Tyr Gly Glu Thr Gly Arg Trp Ile Phe Ala Ala
                165                 170                 175

Gly Ala Phe Ala Ala Ser Leu Val Trp Phe Pro Leu Val Gly Tyr Gly
            180                 185                 190

Ala Ala Ala Leu Ser Arg Pro Leu Ser Ser Pro Arg Val Trp Arg Trp
        195                 200                 205

Ile Asn Ile Gly Val Ala Val Val Leu Thr Gly Leu Ala Val Lys Leu
    210                 215                 220

Ile Leu Met Gly
225

<210> SEQ ID NO 10
<211> LENGTH: 228
<212> TYPE: PRT
<213> ORGANISM: Corynebacterium diphteriae NCTC13129
<220> FEATURE:
<221> NAME/KEY: LysE
<222> LOCATION: (1)..(228)

<400> SEQUENCE: 10

Met Ser Ile Ala Ile Ala Gly Phe Leu Met Gly Leu Ser Leu Ile Val
1               5                   10                  15

Ala Ile Gly Pro Gln Asn Ala Leu Ile Ile Arg Gln Gly Ile Lys Arg
            20                  25                  30

Glu Gly Leu Ile Pro Ile Leu Val Cys Ile Leu Ser Asp Val Ile
        35                  40                  45

Leu Ile Phe Gly Gly Thr Ala Gly Val Gly Ala Leu Val Asp Arg Ala
    50                  55                  60

Pro Ile Ala Leu Val Val Leu Lys Trp Leu Gly Val Ala Tyr Leu Leu
65                  70                  75                  80

Tyr Phe Gly Phe Thr Cys Phe Lys Glu Ala Phe Lys Arg His Gly Gln
                85                  90                  95

Ala Leu Ala Val Glu Gln Ser Glu Pro Val Ala Tyr Glu Pro Val Ala
            100                 105                 110

Asp Ala Ser Ser Gly Val Ile Thr Lys Thr Arg Thr Lys Ala Gln Pro
        115                 120                 125

Lys Ser Ala Gln Arg Thr Trp Val Lys Pro Val Leu Ala Ala Leu Ala
    130                 135                 140

Phe Thr Trp Leu Asn Pro Ala Ala Tyr Ile Asp Val Leu Val Met Leu
145                 150                 155                 160

Gly Gly Ile Ala Asn Gln His Gly Pro Asp Gly Arg Trp Val Phe Ala
                165                 170                 175

Leu Gly Ala Leu Cys Ala Ser Leu Thr Trp Phe Pro Phe Ile Gly Tyr
            180                 185                 190

Thr Ser Thr Arg Phe Ser Thr Val Leu Ser Arg Pro Ala Val Trp Arg
        195                 200                 205

Tyr Ile Asn Ile Ala Ile Gly Ile Ile Met Met Ile Met Cys Ala Arg
    210                 215                 220

Leu Ile Met His
225

<210> SEQ ID NO 11
<211> LENGTH: 222
<212> TYPE: PRT
<213> ORGANISM: Corynebacterium striatum ATCC6940
<220> FEATURE:
<221> NAME/KEY: LysE
<222> LOCATION: (1)..(222)
```

-continued

<400> SEQUENCE: 11

```
Met Ser Val Leu Leu Ala Gly Phe Leu Gly Leu Ser Leu Ile Val
1               5                   10                  15

Ala Ile Gly Pro Gln Asn Ala Tyr Ile Ile Lys Met Gly Val Lys Arg
            20                  25                  30

Asp His Ile Gly Ala Ile Ile Leu Ala Cys Leu Leu Ser Asp Val Ile
            35                  40                  45

Leu Ile Asn Ala Gly Val Gly Met Gly Val Leu Val Glu Lys Phe
    50                  55                  60

Pro Thr Gly Leu Ile Ile Met Lys Tyr Leu Gly Ala Ala Tyr Leu Ile
65                  70                  75                  80

Tyr Phe Gly Phe Thr Cys Phe Arg Asp Ala Phe Lys Lys Glu Gln Glu
                85                  90                  95

Ala Leu Val Val Ser Ser Thr Pro Ser Ala Pro Asn Glu Thr Glu
            100                 105                 110

Leu Gly Gly Ala Thr Thr Val Met Thr Lys Gln Arg Thr Lys Ser Arg
        115                 120                 125

Thr Trp Val Lys Pro Val Met Gly Ala Met Ala Leu Thr Trp Leu Asn
130                 135                 140

Pro Leu Ala Tyr Val Asp Val Leu Val Met Leu Gly Gly Ile Ala Gln
145                 150                 155                 160

His Tyr Gly Asp Gln Arg Trp Val Phe Ala Ala Gly Ala Ile Met Ala
                165                 170                 175

Ser Ala Val Trp Phe Pro Thr Val Gly Tyr Gly Ala Phe Lys Leu Ser
            180                 185                 190

His Val Leu Ala Lys Pro Thr Thr Trp Arg Tyr Val Asn Phe Ala Ile
        195                 200                 205

Gly Cys Val Met Met Leu Leu Thr Ala Lys Leu Leu Leu His
    210                 215                 220
```

<210> SEQ ID NO 12
<211> LENGTH: 235
<212> TYPE: PRT
<213> ORGANISM: Corynebacterium aurimucosum ATCC700975
<220> FEATURE:
<221> NAME/KEY: LysE
<222> LOCATION: (1)..(235)

<400> SEQUENCE: 12

```
Met Arg Arg Leu Glu Ala Met Ser Val Leu Leu Ala Gly Phe Ala Leu
1               5                   10                  15

Gly Leu Ser Leu Ile Ile Ala Ile Gly Pro Gln Asn Ala Tyr Ile Ile
            20                  25                  30

Lys Met Gly Ile Lys Arg Asp His Val Gly Pro Ile Leu Leu Ala Cys
        35                  40                  45

Leu Leu Ser Asp Val Ile Leu Ile Thr Gly Thr Ala Gly Val Gly
    50                  55                  60

Val Leu Val Glu Arg Phe Pro Thr Ala Leu Val Val Lys Tyr Leu
65                  70                  75                  80

Gly Ala Ala Tyr Leu Ile Tyr Phe Gly Phe Thr Cys Phe Arg Asp Ala
                85                  90                  95

Phe Lys Lys Gln Gln Asp Ala Leu Val Ile Glu Thr Thr Pro Val
            100                 105                 110

Ala Gln Val Val Asp Glu Asn Ser Gly Asn Ala Gly Ala Pro Gly Thr
        115                 120                 125

Ser Val Leu Thr Lys Ile Arg Pro Arg Val Arg Ser Lys Ser Trp Val
```

```
            130                 135                 140
Lys Pro Val Leu Gly Ala Leu Ala Leu Thr Trp Leu Asn Pro Leu Ala
145                 150                 155                 160

Tyr Val Asp Ala Leu Val Met Leu Gly Ser Ile Ala Asn Gln Tyr Gly
                    165                 170                 175

Asp Gln Arg Trp Val Phe Ala Gly Ala Ile Leu Ala Ser Ala Val
                180                 185                 190

Trp Phe Pro Ser Leu Gly Phe Gly Ala Tyr Lys Leu Ser His Val Leu
                195                 200                 205

Ala Lys Pro Thr Thr Trp Arg Val Val Asn Ile Val Ile Gly Cys Val
210                 215                 220

Met Leu Ala Leu Thr Ala Lys Leu Leu Phe Leu
225                 230                 235
```

<210> SEQ ID NO 13
<211> LENGTH: 244
<212> TYPE: PRT
<213> ORGANISM: Corynebacterium matruchotii ATCC33806
<220> FEATURE:
<221> NAME/KEY: LysE
<222> LOCATION: (1)..(244)

<400> SEQUENCE: 13

```
Met Ser Ile Ala Val Ala Gly Phe Leu Leu Gly Leu Ser Leu Ile Val
1               5                   10                  15

Ala Ile Gly Pro Gln Asn Ala Leu Val Ile Arg Gln Gly Val Lys Arg
                20                  25                  30

Glu Gly Leu Ile Val Val Leu Ala Ile Cys Ile Leu Ser Asp Ile Phe
            35                  40                  45

Leu Ile Phe Gly Gly Thr Ala Gly Val Gly Val Ile Ile Glu Lys Ala
        50                  55                  60

Pro Leu Ala Leu Val Ala Leu Lys Trp Phe Gly Ala Ala Tyr Leu Ala
65                  70                  75                  80

Trp Phe Ala Val Ser Cys Phe Arg Asp Met Val Lys Pro Arg Ala Leu
                85                  90                  95

Asp Ser Ser Ala Thr Asp Asp Gly Thr Ser Leu Asp Asp Ala Pro Thr
                100                 105                 110

Ala Ala His Val Ser Asn Val Asp Thr Thr Ser Gly Asn Gly Gly Gln
            115                 120                 125

Val Gln Thr Lys Thr Arg Pro Ile Thr Thr Thr Ala Pro Thr Arg Gln
        130                 135                 140

Ala His Pro Ala Arg Pro Trp Val Lys Pro Ala Leu Ala Leu Ala
145                 150                 155                 160

Phe Thr Trp Leu Asn Pro Ser Ala Tyr Ile Asp Thr Leu Val Met Leu
                165                 170                 175

Gly Gly Ile Ala Asn Gln His Gly Glu Ser Gly Arg Trp Val Phe Ala
            180                 185                 190

Ala Gly Ala Leu Met Ala Ser Ala Val Trp Phe Pro Leu Leu Gly Phe
        195                 200                 205

Phe Ser Thr Arg Phe Ser Arg Val Leu Ser Arg Pro Gln Ala Trp Arg
210                 215                 220

Val Ile Asn Gly Val Ile Gly Cys Ile Met Val Val Met Cys Ile Arg
225                 230                 235                 240

Leu Val Met His
```

<210> SEQ ID NO 14

```
<211> LENGTH: 230
<212> TYPE: PRT
<213> ORGANISM: Corynebacterium pseudogenitalium ATCC33035
<220> FEATURE:
<221> NAME/KEY: LysE
<222> LOCATION: (1)..(230)

<400> SEQUENCE: 14
```

Met Ser Ile Val Leu Ala Gly Phe Phe Leu Gly Leu Ser Leu Ile Val
1               5                   10                  15

Ala Val Gly Pro Gln Asn Ala Met Leu Leu Lys Tyr Gly Ile Arg Arg
            20                  25                  30

Asp His Ile Gly Leu Ile Ile Val Val Cys Ala Leu Ser Asp Val Ile
        35                  40                  45

Leu Ile Thr Ser Gly Thr Ala Gly Val Gly Tyr Leu Val Glu Lys Phe
    50                  55                  60

Pro Asn Ala Leu Gln Val Leu Lys Tyr Val Gly Ala Ala Tyr Leu Ala
65                  70                  75                  80

Tyr Phe Thr Phe Thr Cys Phe Arg Asp Ala Phe Lys Thr Lys Gly Glu
                85                  90                  95

Ala Ile Glu Val Glu Ser Thr Gln Pro Lys Ala Pro Gln Glu Val Ala
            100                 105                 110

Ser Phe Asp Gly Ser Gln Ala Arg Ser Thr Thr Lys Thr Ala Ala Arg
        115                 120                 125

Val Glu Ile Lys Arg Ser Pro Ser Trp Val Lys Pro Leu Leu Thr Ala
    130                 135                 140

Leu Ala Leu Thr Trp Leu Asn Pro Gly Ala Tyr Val Asp Val Val Val
145                 150                 155                 160

Met Leu Gly Ser Ile Ala Asn Gln Tyr Gly Glu Ser Gly Arg Trp Leu
                165                 170                 175

Phe Ala Val Gly Ala Ile Cys Ala Ser Phe Thr Trp Phe Pro Phe Ile
            180                 185                 190

Gly Phe Gly Ala Ala Arg Phe Ser His Val Leu Ser Arg Pro Thr Val
        195                 200                 205

Trp Arg Trp Ile Asn Phe Gly Ile Gly Val Ile Met Ile Gly Leu Thr
    210                 215                 220

Leu Lys Leu Leu Leu Leu
225                 230

```
<210> SEQ ID NO 15
<211> LENGTH: 241
<212> TYPE: PRT
<213> ORGANISM: Corynebacterium accolens ATCC49725
<220> FEATURE:
<221> NAME/KEY: LysE
<222> LOCATION: (1)..(241)

<400> SEQUENCE: 15
```

Met Ser Ile Val Leu Ala Gly Phe Val Leu Gly Leu Ser Leu Ile Val
1               5                   10                  15

Ala Val Gly Pro Gln Asn Ala Met Leu Leu Lys Tyr Gly Ile Arg Arg
            20                  25                  30

Asp His Ile Gly Leu Ile Ile Val Val Cys Ala Leu Ser Asp Val Ile
        35                  40                  45

Leu Ile Thr Ser Gly Thr Ala Gly Val Gly Tyr Leu Val Glu Arg Phe
    50                  55                  60

Pro Asn Ala Leu Glu Ala Leu Lys Tyr Ile Gly Ala Ala Tyr Leu Ala
65                  70                  75                  80

```
Phe Phe Thr Phe Thr Cys Phe Arg Asp Ala Phe Lys Thr Lys Gly Glu
                85                  90                  95

Ala Ile Asp Val Glu Ser Thr Ser Pro Asn Ser Thr Glu Glu Val Ala
            100                 105                 110

Thr Phe Asp Gly Asp Gly Asp Ser Thr Gly Gly Val Gly Thr Glu His
        115                 120                 125

Gly Ser Val Ala Thr Ala Thr Thr Gln Arg Gln Glu Ile Lys Arg
130                 135                 140

Ser Pro Ser Trp Val Lys Pro Leu Leu Thr Ala Leu Ala Leu Thr Trp
145                 150                 155                 160

Leu Asn Pro Gly Ala Tyr Val Asp Val Leu Val Met Leu Gly Gly Ile
                165                 170                 175

Ala Asn Gln Tyr Gly Asp Pro Gly Arg Trp Leu Phe Ala Gly Gly Ala
            180                 185                 190

Ile Ala Ala Ser Phe Thr Trp Phe Pro Val Ile Gly Phe Gly Ala Ala
        195                 200                 205

Arg Phe Ser His Val Leu Ser Arg Pro Glu Val Trp Arg Trp Ile Asn
210                 215                 220

Val Gly Ile Gly Val Ile Met Ile Gly Leu Thr Leu Lys Leu Leu Leu
225                 230                 235                 240

Leu
```

<210> SEQ ID NO 16
<211> LENGTH: 261
<212> TYPE: PRT
<213> ORGANISM: Corynebacterium glucuronalyticum ATCC51867

<400> SEQUENCE: 16

```
Met Val Pro Glu Asn Leu Ser Phe Tyr Leu Cys Val Leu Leu Thr His
1               5                   10                  15

Asn Lys Tyr Val Asn Val Phe Phe Ala Gly Leu Leu Phe Asn Leu Ser
            20                  25                  30

Leu Ile Leu Ala Leu Gly Pro Gln Asn Ala Leu Ile Leu Lys Tyr Gly
        35                  40                  45

Leu Arg Arg Gln Ala Ile Thr Leu Val Ile Ser Val Cys Ala Leu Cys
50                  55                  60

Asp Ile Thr Leu Ile Ala Leu Ser Gly Val Gly Val Gly Val Ile Leu
65                  70                  75                  80

Gln Lys Ala Pro Ile Val Leu Glu Ile Leu Arg Tyr Ala Gly Phe Leu
                85                  90                  95

Tyr Leu Leu Trp Phe Ala Tyr Thr Cys Phe Arg Asp Ala Ile His Pro
            100                 105                 110

Lys Thr Leu Ala Thr Glu Thr Val Ser Glu Thr Lys Pro His Glu Glu
        115                 120                 125

Glu Leu Pro Asp Val Ser Ser Thr Thr Ala Gly Thr Thr Met Ala Thr
130                 135                 140

Ala Thr Val Met Glu Thr Ala Thr Thr Val Lys Glu Lys Thr His Arg
145                 150                 155                 160

Arg Thr Phe His Ile Pro Gln Glu Ile Lys Gly Pro Ala Val Ala Ala
                165                 170                 175

Phe Val Val Ser Val Ile Asn Pro Ala Ala Trp Val Asp Leu Phe Val
            180                 185                 190

Val Ile Gly Ser Ile Ser Ser Ser Tyr Gly Pro Asp Lys Trp Ala Phe
        195                 200                 205

Leu Leu Gly Thr Met Ala Ala Ser Leu Val Trp Phe Pro Ala Phe Gly
```

```
              210                 215                 220
Tyr Gly Ala Ala Ala Leu Ser Arg Pro Leu Ser Ser Pro Lys Val Trp
225                 230                 235                 240

Arg Cys Ile Asn Thr Gly Ile Gly Leu Phe Met Val Phe Met Ala Phe
            245                 250                 255

Arg Val Leu Phe Met
            260

<210> SEQ ID NO 17
<211> LENGTH: 204
<212> TYPE: PRT
<213> ORGANISM: Micrococcus luteus NCTC2665

<400> SEQUENCE: 17

Met Trp Thr Leu Ala Gly Thr Gly Leu Leu Thr Gly Leu Ala Leu Ile
1               5                   10                  15

Val Ala Ile Gly Ala Gln Asn Ala Phe Val Leu Arg Gln Gly Val Arg
            20                  25                  30

Arg Glu His Val Gly Ala Val Val Leu Val Cys Met Ala Ser Asp Ala
        35                  40                  45

Val Leu Ile Leu Ala Gly Thr Ala Gly Val Gly Ala Leu Val Gln Ala
    50                  55                  60

Val Pro Trp Leu Leu Glu Val Leu Arg Trp Gly Gly Ala Leu Tyr Leu
65                  70                  75                  80

Leu Trp Phe Ala Val Ser Ser Leu Arg Ala Ala Leu Arg Pro Gln Gly
                85                  90                  95

Leu Met Ala Glu Gln Ala Pro Arg Thr Ala Gly Ser Val Ile Ala Thr
            100                 105                 110

Thr Leu Ala Leu Thr Trp Leu Asn Pro His Val Tyr Leu Asp Thr Val
        115                 120                 125

Val Leu Leu Gly Ser Leu Ala Asn Gln His Gly Pro Asp Ala Arg Trp
    130                 135                 140

Val Phe Ala Ala Gly Ala Val Ala Ala Ser Val Leu Trp Phe Thr Ala
145                 150                 155                 160

Leu Gly Tyr Gly Ala Arg Leu Leu Ala Arg Val Leu Ala Asp Pro Lys
                165                 170                 175

Ala Trp Arg Val Val Asp Val Val Ile Ala Val Val Met Ala Val Leu
            180                 185                 190

Ala Val Arg Leu Ile Ala Gly Ser Asp Val Trp Gly
        195                 200

<210> SEQ ID NO 18
<211> LENGTH: 230
<212> TYPE: PRT
<213> ORGANISM: Corynebacterium tubuculostearicum SK141
<220> FEATURE:
<221> NAME/KEY: ArgO(LysE)
<222> LOCATION: (1)..(230)

<400> SEQUENCE: 18

Met Ser Ile Val Leu Ala Gly Phe Phe Leu Gly Leu Ser Leu Ile Val
1               5                   10                  15

Ala Val Gly Pro Gln Asn Ala Met Leu Leu Lys Tyr Gly Ile Arg Arg
            20                  25                  30

Asp His Ile Gly Leu Ile Ile Val Cys Ala Leu Ser Asp Val Ile
        35                  40                  45

Leu Ile Thr Ser Gly Thr Ala Gly Val Gly Tyr Leu Val Glu Lys Phe
    50                  55                  60
```

Pro Asn Ala Leu Gln Val Leu Lys Tyr Val Gly Ala Ala Tyr Leu Ala
65                  70                  75                  80

Tyr Phe Thr Phe Thr Cys Phe Arg Asp Ala Leu Lys Thr Lys Gly Glu
            85                  90                  95

Ala Ile Glu Val Glu Ser Thr Gln Pro Lys Val Pro Gln Glu Val Ala
        100                 105                 110

Ser Phe Asp Gly Ser Gln Ala Arg Asn Thr Thr Lys Thr Ala Thr Arg
    115                 120                 125

Val Glu Ile Lys Arg Ser Pro Ser Trp Val Lys Pro Leu Leu Thr Ala
130                 135                 140

Leu Ala Leu Thr Trp Leu Asn Pro Gly Ala Tyr Val Asp Val Val Val
145                 150                 155                 160

Met Leu Gly Ser Ile Ala Asn Gln Tyr Gly Glu Ser Gly Arg Trp Leu
                165                 170                 175

Phe Ala Val Gly Ala Ile Cys Ala Ser Phe Thr Trp Phe Pro Phe Ile
            180                 185                 190

Gly Phe Gly Ala Ala Arg Phe Ser His Val Leu Ser Arg Pro Thr Val
        195                 200                 205

Trp Arg Trp Ile Asn Phe Gly Ile Gly Val Ile Met Ile Gly Leu Thr
210                 215                 220

Leu Lys Leu Leu Leu Leu
225                 230

<210> SEQ ID NO 19
<211> LENGTH: 244
<212> TYPE: PRT
<213> ORGANISM: Corynebacterium matruchotii ATCC14266
<220> FEATURE:
<221> NAME/KEY: ArgO(LysE)
<222> LOCATION: (1)..(244)

<400> SEQUENCE: 19

Met Ser Ile Ala Val Ala Gly Phe Leu Leu Gly Leu Ser Leu Ile Val
1               5                   10                  15

Ala Ile Gly Pro Gln Asn Ala Leu Val Ile Arg Gln Gly Val Lys Arg
            20                  25                  30

Glu Gly Leu Ile Val Val Leu Ala Ile Cys Met Leu Ser Asp Ile Phe
        35                  40                  45

Leu Ile Phe Gly Gly Thr Ala Gly Val Gly Val Ile Ile Glu Lys Ala
    50                  55                  60

Pro Leu Ala Leu Val Ala Leu Lys Trp Phe Gly Ala Ala Tyr Leu Ala
65                  70                  75                  80

Trp Phe Ala Val Ser Cys Phe Lys Asp Met Val Lys Pro Arg Ala Leu
            85                  90                  95

Asp Ser Ser Ala Thr Asp Asn Gly Thr Ser Leu Asp Asp Ala Pro Thr
        100                 105                 110

Val Ala His Ile Ser Asn Val Asp Ser Thr Ser Gly Asn Gly Gly Gln
    115                 120                 125

Val Gln Thr Lys Thr Arg Pro Ile Thr Thr Ala Pro Thr Arg Gln
130                 135                 140

Ala His Pro Ala Arg Pro Trp Val Lys Pro Ala Leu Ala Ala Leu Ala
145                 150                 155                 160

Phe Thr Trp Leu Asn Pro Ser Ala Tyr Ile Asp Thr Leu Val Met Leu
                165                 170                 175

Gly Gly Ile Ala Asn Gln His Gly Glu Ser Gly Arg Trp Val Phe Ala
            180                 185                 190

```
Ala Gly Ala Leu Met Ala Ser Ala Val Trp Phe Pro Leu Leu Gly Phe
            195                 200                 205

Phe Ser Thr Arg Phe Ser Arg Val Leu Ser Arg Pro Gln Ala Trp Arg
        210                 215                 220

Val Ile Asn Gly Val Ile Gly Cys Ile Met Val Met Cys Ile Arg
225                 230                 235                 240

Leu Ile Met His
```

<210> SEQ ID NO 20
<211> LENGTH: 864
<212> TYPE: DNA
<213> ORGANISM: Corynebacterium glutamicum ATCC13032
<220> FEATURE:
<221> NAME/KEY: lysE
<222> LOCATION: (76)..(777)
<223> OTHER INFORMATION: pVWEx1- Insert

<400> SEQUENCE: 20

```
tgagcggata caatttcac acaggaaaca gaattaaaag atatgaccat gattacgcca      60
agcttgcatg ccatcatgga aatcttcatt acaggtctgc ttttgggggc cagtcttta    120
ctgtccatcg gaccgcagaa tgtactggtg attaaacaag gaattaagcg cgaaggactc   180
attgcggttc ttctcgtgtg tttaatttct gacgtctttt tgttcatcgc cggcaccttg   240
ggcgttgatc ttttgtccaa tgccgcgccg atcgtgctcg atattatgcg ctggggtggc   300
atcgcttacc tgttatggtt tgccgtcatg gcagcgaaag acgccatgac aaacaaggtg   360
gaagcgccac agatcattga agaaacagaa ccaaccgtgc ccgatgacac gcctttgggc   420
ggttcggcgg tggccactga cacgcgcaac cgggtgcggg tggaggtgag cgtcgataag   480
cagcgggttt gggtaaagcc catgttgatg gcaatcgtgc tgacctggtt gaacccgaat   540
gcgtatttgg acgcgtttgt gtttatcggc ggcgtcggcg cgcaatacgg cgacaccgga   600
cggtggattt tcgccgctgg cgcgttcgcg gcaagcctga tctggttccc gctggtgggt   660
ttcggcgcag cagcattgtc acgcccgctg tccagcccca aggtgtggcg ctggatcaac   720
gtcgtcgtgg cagttgtgat gaccgcattg gccatcaaac tgatgttgat gggttagttt   780
tcgcgggttt tggaatcggt ggccttcgcc caaatattga cctagaggat ccccgggtac   840
cgagctcgaa ttcactggcc gtcg                                          864
```

<210> SEQ ID NO 21
<211> LENGTH: 1036
<212> TYPE: DNA
<213> ORGANISM: Corynebacterium glutamicum ATCC13032
<220> FEATURE:
<221> NAME/KEY: 'argD
<222> LOCATION: (15)..(491)
<223> OTHER INFORMATION: 3'-End of argD-Gens
<220> FEATURE:
<221> NAME/KEY: argF'
<222> LOCATION: (505)..(523)
<223> OTHER INFORMATION: 5'-End of argF-Gens
<220> FEATURE:
<221> NAME/KEY: 'argH
<222> LOCATION: (524)..(538)
<223> OTHER INFORMATION: 3'-End of argH-Gens
<220> FEATURE:
<221> NAME/KEY: cg1589'
<222> LOCATION: (605)..(1024)
<223> OTHER INFORMATION: 5'-End of cg1589-Leserasters

<400> SEQUENCE: 21

```
ggtggtgcta gcccggcgat ttctttgcac atcagcacga tggcgttgtt cccgatgtgg      60
```

```
tgaccatggc caagggactt ggcggcggtc ttcccatcgg tgcttgtttg gccactggcc    120
gtgcagctga attgatgacc ccaggcaagc acggcaccac tttcggtggc aacccagttg    180
cttgtgcagc tgccaaggca gtgctgtctg ttgtcgatga cgctttctgc gcagaagttg    240
cccgcaaggg cgagctgttc aaggaacttc ttgccaaggt tgacggcgtt gtagacgtcc    300
gtggcagggg cttgatgttg ggcgtggtgc tggagcgcga cgtcgcaaag caagctgttc    360
ttgatggttt taagcacggc gttattttga atgcaccggc ggacaacatt atccgtttga    420
ccccgccgct ggtgatcacc gacgaagaaa tcgcagacgc agtcaaggct attgccgaga    480
caatcgcata aaggactcaa acttatgact tcacaaccac aggggggtac gtcgataagc    540
attagtttat ggcctgtgct gctttccgat tgcgggagtt gcacaggcca tttattatca    600
attcatgaat ggttcccctg attactcaag aaaatctcga ggcaggggat tttccgtatt    660
tttaggcatc atcctgctgg tcatcgcggt attagcggtc ttggtgggcc gcggaaccat    720
cgccatgcca aagctcttcg gatcaagtaa cttgaccgag gtcagagcag taattggctc    780
ggaaaagaag gaattcttcg aagatccaga agtcgttgaa gccttcgccg accacggctt    840
tgaagttaac gtggacaccg caggatctcg tcggatcgcc actgatgtgg acttgagccc    900
gtacgatttc gcgttcccat cctctgcacc agctgcgcag aagatctccg aagccaacac    960
cacgacgggc cgattcaccc cattctattc gcctatggcg gtagcaacat tcggaaccat   1020
caccatgcat accacc                                                   1036
```

<210> SEQ ID NO 22
<211> LENGTH: 28
<212> TYPE: DNA
<213> ORGANISM: Oligonucleotide
<220> FEATURE:
<221> NAME/KEY: lysE_1.p
<222> LOCATION: (1)..(28)

<400> SEQUENCE: 22

```
tcgatatcat ggaaatcttc attacagg                                        28
```

<210> SEQ ID NO 23
<211> LENGTH: 32
<212> TYPE: DNA
<213> ORGANISM: Oligonucleotide
<220> FEATURE:
<221> NAME/KEY: lysE_2.p
<222> LOCATION: (1)..(32)

<400> SEQUENCE: 23

```
tgcctaggtc aatatttggg cgaaggccac cg                                   32
```

<210> SEQ ID NO 24
<211> LENGTH: 32
<212> TYPE: DNA
<213> ORGANISM: Oligonucleotide
<220> FEATURE:
<221> NAME/KEY: argFRGH_d1
<222> LOCATION: (1)..(32)

<400> SEQUENCE: 24

```
ggtggtgcta gcccggcgat ttctttgcac at                                   32
```

<210> SEQ ID NO 25
<211> LENGTH: 40
<212> TYPE: DNA
<213> ORGANISM: Oligonucleotide
<220> FEATURE:
<221> NAME/KEY: argFRGH_d2

```
<222> LOCATION: (1)..(40)

<400> SEQUENCE: 25
aatgcttatc gacgtacccc cctgtggttg tgaagtcata                                40

<210> SEQ ID NO 26
<211> LENGTH: 20
<212> TYPE: DNA
<213> ORGANISM: Oligonucleotide
<220> FEATURE:
<221> NAME/KEY: argFRGH_d3
<222> LOCATION: (1)..(20)

<400> SEQUENCE: 26
ggggtacgtc gataagcatt                                                     20

<210> SEQ ID NO 27
<211> LENGTH: 32
<212> TYPE: DNA
<213> ORGANISM: Oligonucleotide
<220> FEATURE:
<221> NAME/KEY: argFRGH_d4
<222> LOCATION: (1)..(32)

<400> SEQUENCE: 27
ggtggtatgc atggtgatgg ttccgaatgt tg                                       32

<210> SEQ ID NO 28
<211> LENGTH: 238
<212> TYPE: DNA
<213> ORGANISM: PgapRBS Corynebacterium glutamicum ATCC13032
<220> FEATURE:
<221> NAME/KEY: RBS
<222> LOCATION: (225)..(232)

<400> SEQUENCE: 28
ctgtatgatt tgcatctgc tgcgaaatct ttgtttcccc gctaaagttg aggacaggtt          60
gacacggagt tgactcgacg aattatccaa tgtgagtagg tttggtgcgt gagttggaaa        120
aattcgccat actcgccctt gggttctgtc agctcaagaa ttcttgagtg accgatgctc        180
tgattgacct aactgcttga cacattgcat ttcctacaat ctttagagga gacacaac          238

<210> SEQ ID NO 29
<211> LENGTH: 8281
<212> TYPE: DNA
<213> ORGANISM: pEC7lysE

<400> SEQUENCE: 29
tcccagaggc agcgtcggcg gctcctgcct ccccgcccg cgccgaccg ggacccgcaa           60 accccttgat ccgctgtcgg gggtgatcct gcaagcctcg tcgtcctggc cggaccacgc        120
tatctgtgca aggtccccgg ccccggacgc gcgctccatg agcagagcgc ccgccgggga        180
tcgatccggg cttatcgact gcacggtgca ccaatgcttc tggcgtcagg cagccatcgg        240
aagctgtggt atggctgtgc aggtcgtaaa tcactgcata attcgtgtcg ctcaaggcgc        300
actcccgttc tggataatgt ttttgcgcc gacatcataa cggttctggc aaatattctg        360
aaatgagctg ttgacaatta atcatcggct cgtataatgt gtggaattgt gagcggataa       420
caatttcaca caggaaacag aattcccagc ttgagtagga caaatccgcc gagcttcgac        480
gagattttca ggagctaagg aagctaaaat ggagaaaaaa atcactggat ataccaccgt        540
tgatatatcc caatggcatc gtaaagaaca ttttgaggca tttcagtcag ttgctcaatg        600
tacctataac cagaccgttc agctggatat tacggccttt ttaaagaccg taaagaaaaa        660
```

```
taagcacaag ttttatccgg cctttattca cattcttgcc cgcctgatga atgctcatcc    720
ggaattccgt atggcaatga aagacggtga gctggtgata tgggatagtg ttcacccttg    780
ttacaccgtt ttccatgagc aaactgaaac gttttcatcg ctctggagtg aataccacga    840
cgatttccgg cagtttctac acatatattc gcaagatgtg gcgtgttacg gtgaaaacct    900
ggcctatttc cctaaagggt ttattgagaa tatgtttttc gtctcagcca atccctgggt    960
gagtttcacc agttttgatt taaacgtggc caatatggac aacttcttcg cccccgtttt   1020
caccatgggc aaatattata cgcaaggcga caaggtgctg atgccgctgg cgattcaggt   1080
tcatcatgcc gtttgtgatg cttccatgt cggcagaatg cttaatgaat tacaacagta    1140
ctgcgatgag tggcagggcg gggcgtaatt ttttaaggc agttattggt gcccttaaac     1200
gcctggttgc tacgcctgaa taagtgataa taagcggatg aatggcagaa attcgtcgag   1260
gcggcacctc gctaacggat tcaccactcc aagaattgga gccaatcaat tcttgcggag   1320
aactgtgaat gcgcaaacca acccttggca gaacatatcc atcgcgtccg ccatctccag   1380
cagccgcacg cggcgcatct cggctgtttt ggcggatgag agaagatttt cagcctgata   1440
cagattaaat cagaacgcag aagcggtctg ataaaacaga atttgcctgg cggcagtagc   1500
gcggtggtcc cacctgaccc catgccgaac tcagaagtga acgccgtag cgccgatggt    1560
agtgtgggt ctcccatgc gagagtaggg aactgccagg catcaaataa acgaaaggc      1620
tcagtcgaaa gactgggcct ttcgttttat ctgttgtttg tcggtgaacg ctctcctgag   1680
taggacaaat ccgccgggag cggatttgaa cgttgcgaag caacggcccg gagggtggcg   1740
ggcaggacgc ccgccataaa ctgccaggca tcaaattaag cagaaggcca tcctgacgga   1800
tggccttttt gcgtttctac aaactcttcc tgtcgtcata tctacaagcc atcccccac    1860
agatacggta aactagcctc gttttttgcat caggaaagca gaattcgtaa tcatgtcata   1920
gctgttcct gtgtgaaatt gttatccgct cacaattcca cacacatac gagccggaag     1980
cataaagtgt aaagcctggg gtgcctaatg agtgagctaa ctcacattaa ttgcgttgcg   2040
ctcactgccc gctttccagt cgggaaacct gtcgtgccag ctgcattaat gaatcggcca   2100
acgcgcgggg agaggcggtt tgcgtattgg gcgctcttcc gcttcctcgc tcactgactc   2160
gctgcgctcg gtcgttcggc tgcggcgagc ggtatcagct cactcaaagg cggtaatacg   2220
gttatccaca gaatcagggg ataacgcagg aaagaacatg tgagcaaaag gccagcaaaa   2280
ggccaggaac cgtaaaaagg ccgcgttgct ggcgtttttc cataggctcc gcccccctga   2340
cgagcatcac aaaaatcgac gctcaagtca gaggtggcga aacccgacag gactataaag   2400
ataccaggcg tttccccctg gaagctccct cgtgcgctct cctgttccga ccctgccgct   2460
taccggatac ctgtccgcct ttctcccttc gggaagcgtg gcgctttctc atagctcacg   2520
ctgtaggtat ctcagttcgg tgtaggtcgt tcgctccaag ctgggctgtg tgcacgaacc   2580
ccccgttcag cccgaccgct gcgccttatc cggtaactat cgtcttgagt ccaacccggt   2640
aagacacgac ttatcgccac tggcagcagc cactggtaac aggattagca gagcgaggta   2700
tgtaggcggt gctacagagt tcttgaagtg gtggcctaac tacggctaca ctagaagaac   2760
agtatttggt atctgcgctc tgctgaagcc agttaccttc ggaaaaagag ttggtagctc   2820
ttgatccggc aaacaaacca ccgctggtag cggtggtttt tttgtttgca agcagcagat   2880
tacgcgcaga aaaaaaggat ctcaagaaga tcctttgatc ttttctacgg ggtctgacgc   2940
tcagtggaac gaaaactcac gttaagggat tttggtcatg agattatcaa aaaggatctt   3000
cacctagatc cttttggggg gggggggaaa gccacgttgt gtctcaaaat ctctgatgtt   3060
```

```
acattgcaca agataaaaat atatcatcat gaacaataaa actgtctgct tacataaaca   3120
gtaatacaag gggtgttatg agccatattc aacgggaaac gtcttgctcg aagcccgcct   3180
aatgagcggg cttttttta aaaaaagcc cgctcattag gcgggctagc ccgcctaatg    3240
agcgggcttt ttttttcgag gccgcgatta aattccaaca tggatgctga tttatatggg   3300
tataaatggg ctcgaaaaga tatgaccatg attacgccaa gcttgcatgc ctgcaggtcg   3360
actctagagg atccaccgtg accagtgcat tgattggtgc ttcgtcagtt gagcagctgg   3420
acaacagcct tgattcactc aacaacttgg agttttctga cgccgagttg gaggcgatcg   3480
atgagatttc ccacgacgcc ggcatcaaca tttgggcgaa ggccaccgat tccaaaaccc   3540
gcgaaaacta acccatcaac atcagtttga tggccaatgc ggtcatcaca actgccacga   3600
cgacgttgat ccagcgccac accttggggc tggacagcgg gcgtgacaat gctgctgcgc   3660
cgaaacccac cagcgggaac cagatcaggc ttgccgcgaa cgcgccagcg gcgaaaatcc   3720
accgtccggt gtcgccgtat tgcgcgccga cgccgccgat aaacacaaac gcgtccaaat   3780
acgcattcgg gttcaaccag gtcagcacga ttgccatcaa catgggcttt acccaaaccc   3840
gctgcttatc gacgctcacc tccacccgca cccggttgcg cgtgtcagtg gccaccgccg   3900
aaccgcccaa aggcgtgtca tcgggcacgg ttggttctgt ttcttcaatg atctgtggcg   3960
cttccacctt gtttgtcatg gcgtctttcg ctgccatgac ggcaaaccat aacaggtaag   4020
cgatgccacc ccagcgcata atatcgagca cgatcggcgc ggcattggac aaaagatcaa   4080
cgcccaaggt gccggcgatg aacaaaaaga cgtcagaaat taaacacacg agaagaaccg   4140
caatgagtcc ttcgcgctta attccttgtt taatcaccag tacattctgc ggtccgatgg   4200
acagtaaaag actggccccc aaaagcagac ctgtaatgaa gatttccatg atcaccatcg   4260
tgacctatgg aagtacttaa gtaaaatgat tggttcttaa catggtttaa tatagcttca   4320
tgaaccccat tcaactggac actttgctct caatcattga tgaaggcagc ttcgaaggcg   4380
cctccttagc ccttttccatt tcccctcgg cggtgagtca gcgcggatcc ccgggtaccg   4440
agctcgaatt cactggccgt cgttttaccg ataatgtcgg gcaatcaggt gcgacaatct   4500
atcgagcttt tgccattctc accggattca gtcgtcactc atggtgattt ctcacttgat   4560
aaccttattt ttgacgaggg gaaattaata ggttgtattg atgttggacg agtcggaatc   4620
gcagaccgat accaggatct tgccatccta tggaactgcc tcggtgagtt ttctccttca   4680
ttacagaaac ggcttttttca aaatatggt attgataatc ctgatatgaa taaattgcag   4740
tttcatttga tgctcgatga gttttttctaa tcagaattgg ttaattggtt gtaacactgg   4800
cagagcatta cgctgacttg acgggacggc ggctttgttg aataaatcga acttttgctg   4860
agttgaagga tcagatcacg catcttcccg acaacgcaga ccgttccgtg gcaaagcaaa   4920
agttcaaaat caccaactgg tccacctaca acaaagctct catcaaccgt ggctccctca   4980
cttttctggct ggatgatggg gcgattcagg cctggtatga gtcagcaaca ccttcttcac   5040
gaggcagacc tcagcgcccc cccccccta gcttgtctac gtctgatgct ttaatcgga    5100
cggacttgcc gatcttgtat gcggtgattt ttccctcgtt tgcccacttt ttaatggtgg   5160
ccggggtgag agctacgcgg gcggcgacct gctgcgctgt gatccaatat tcggggtcgt   5220
tcactggttc cccttttctga tttctggcat agaagaaccc ccgtgaactg tgtggttccg   5280
ggggttgctg attttttgcga gacttctcgc gcaattccct agcttaggtg aaaacaccat   5340
gaaacactag ggaacacccc atgaaacacc cattagggca gtaggcggc ttcttcgtct    5400
agggcttgca tttgggcggt gatctggtct ttagcgtgtg aaagtgtgtc gtaggtggcg   5460
```

```
tgctcaatgc actcgaacgt cacgtcattt accgggtcac ggtggcaaa gagaactagt      5520
gggttagaca ttgttttcct cgttgtcggt ggtggtgagc ttttctagcc gctcggtaaa     5580
cgcggcgatc atgaactctt ggaggttttc accgttctgc atgcctgcgc gcttcatgtc     5640
ctcacgtagt gccaaaggaa cgcgtgcggt gaccacgacg ggcttagcct ttgcctgcgc     5700
ttctagtgct tcgatggtgg cttgtgcctg cgcttgctgc gcctgtagtg cctgttgagc     5760
ttcttgtagt tgctgttcta gctgtgcctt ggttgccatg ctttaagact ctagtagctt     5820
tcctgcgata tgtcatgcgc atgcgtagca aacattgtcc tgcaactcat tcattatgtg     5880
cagtgctcct gttactagtc gtacatactc atatttacct agtctgcatg cagtgcatgc     5940
acatgcagtc atgtcgtgct aatgtgtaaa acatgtacat gcagattgct gggggtgcag     6000
ggggcggagc caccctgtcc atgcggggtg tggggcttgc cccgccggta cagacagtga     6060
gcaccgggc acctagtcgc ggatacccc cctaggtatc ggacacgtaa ccctcccatg       6120
tcgatgcaaa tctttaacat tgagtacggg taagctggca cgcatagcca agctaggcgg     6180
ccaccaaaca ccactaaaaa ttaatagttc ctagacaaga caaaccccg tgcgagctac      6240
caactcatat gcacggggc cataacccc gaagggttt caattgacaa ccatagcact        6300
agctaagaca acgggcacaa cacccgcaca aactcgcact gcgcaacccc gcacaacatc     6360
gggtctaggt aacactgaaa tagaagtgaa cacctcaag gaaccgcagg tcaatgaggg      6420
ttctaaggtc actcgcgcta gggcgtggcg taggcaaaac gtcatgtaca agatcaccaa     6480
tagtaaggct ctggcggggt gccataggtg gcgcagggac gaagctgttg cggtgtcctg    6540
gtcgtctaac ggtgcttcgc agtttgaggg tctgcaaaac tctcactctc gctggggtc     6600
acctctggct gaattggaag tcatgggcga acgccgcatt gagctggcta ttgctactaa    6660
gaatcacttg gcggcgggtg gcgcgctcat gatgtttgtg ggcactgttc gacacaaccg     6720
ctcacagtca tttgcgcagg ttgaagcggg tattaagact gcgtactctt cgatggtgaa     6780
aacatctcag tggaagaaag aacgtgcacg gtacggggtg gagcacacct atagtgacta    6840
tgaggtcaca gactcttggg cgaacggttg gcacttgcac cgcaacatgc tgttgttctt     6900
ggatcgtcca ctgtctgacg atgaactcaa ggcgtttgag gattccatgt tttcccgctg     6960
gtctgctggt gtggttaagg ccggtatgga cgcgccactg cgtgagcacg gggtcaaact     7020
tgatcaggtg tctacctggg gtggagacgc tgcgaaaatg gcaacctacc tcgctaaggg    7080
catgtctcag gaactgactg gctccgctac taaaaccgcg tctaagggt cgtacacgcc      7140
gtttcagatg ttggatatgt tggccgatca aagcgacgcc ggcgaggata tggacgctgt     7200
tttggtggct cggtggcgtg agtatgaggt tggttctaaa aacctgcgtt cgtcctggtc     7260
acgtggggct aagcgtgctt tgggcattga ttacatagac gctgatgtac gtcgtgaaat     7320
ggaagaagaa ctgtacaagc tcgccggtct ggaagcaccg gaacgggtcg aatcaacccg     7380
cgttgctgtt gctttggtga agcccgatga ttggaaactg attcagtctg atttcgcggt     7440
taggcagtac gttctagatt gcgtggataa ggctaaggac gtggccgctg cgcaacgtgt    7500
cgctaatgag gtgctggcaa gtctgggtgt ggattccacc ccgtgcatga tcgttatgga     7560
tgatgtggac ttggacgcgg ttctgcctac tcatggggac gctactaagc gtgatctgaa    7620
tgcggcggtg ttcgcgggta atgagcagac tattcttcgc acccactaaa agcggcataa    7680
accccgttcg atattttgtg cgatgaattt atggtcaatg tcgcggggc aaactatgat     7740
gggtcttgtt gttgacaatg gctgatttca tcaggaatgg aactgtcatg ctgttatgtg     7800
cctggctcct aatcaaagct ggggacaatg ggttgccccg ttgatctgat ctagttcgga    7860
```

```
ttggcggggc ttcactgtat ctgggggtgg catcgtgaat agattgcaca ccgtagtggg    7920
cagtgtgcac accatagtgg ccatgagcac caccacccccc agggacgccg acggcgcgaa    7980
gctctgcgcc tggtgcggct cggagatcaa gcaatccggc gtcggccgga gccgggacta    8040
ctgccgccgc tcctgccgcc agcgggcgta cgaggcccgg cgccagcgcg aggcgatcgt    8100
gtccgccgtg gcgtcggcag tcgctcgccg agatacgtca cgtgacgaaa tgcagcagcc    8160
ttccattccg tcacgtgacg aaactcgggc cgcaggtcag agcacggttc cgcccgctcc    8220
ggccctgccg gaccccggc tgcagctcgc ccggccgccg gtccccctgc cgtccggccc    8280
g                                                                    8281
```

<210> SEQ ID NO 30
<211> LENGTH: 290
<212> TYPE: PRT
<213> ORGANISM: Corynebacterium glutamicum ATCC13032
<220> FEATURE:
<221> NAME/KEY: misc_feature
<222> LOCATION: (1)..(290)
<223> OTHER INFORMATION: Amino acid sequence of Activator protein LysG
      of Corynebacterium glutamicum ATCC13032

<400> SEQUENCE: 30

```
Met Asn Pro Ile Gln Leu Asp Thr Leu Leu Ser Ile Ile Asp Glu Gly
1               5                   10                  15

Ser Phe Glu Gly Ala Ser Leu Ala Leu Ser Ile Ser Pro Ser Ala Val
            20                  25                  30

Ser Gln Arg Val Lys Ala Leu Glu His His Val Gly Arg Val Leu Val
        35                  40                  45

Ser Arg Thr Gln Pro Ala Lys Ala Thr Glu Ala Gly Glu Val Leu Val
    50                  55                  60

Gln Ala Ala Arg Lys Met Val Leu Leu Gln Ala Glu Thr Lys Ala Gln
65                  70                  75                  80

Leu Ser Gly Arg Leu Ala Glu Ile Pro Leu Thr Ile Ala Ile Asn Ala
                85                  90                  95

Asp Ser Leu Ser Thr Trp Phe Pro Pro Val Phe Asn Glu Val Ala Ser
            100                 105                 110

Trp Gly Gly Ala Thr Leu Thr Leu Arg Leu Glu Asp Glu Ala His Thr
        115                 120                 125

Leu Ser Leu Leu Arg Arg Gly Asp Val Leu Gly Ala Val Thr Arg Glu
    130                 135                 140

Ala Asn Pro Val Ala Gly Cys Glu Val Val Glu Leu Gly Thr Met Arg
145                 150                 155                 160

His Leu Ala Ile Ala Thr Pro Ser Leu Arg Asp Ala Tyr Met Val Asp
                165                 170                 175

Gly Lys Leu Asp Trp Ala Ala Met Pro Val Leu Arg Phe Gly Pro Lys
            180                 185                 190

Asp Val Leu Gln Asp Arg Asp Leu Asp Gly Arg Val Asp Gly Pro Val
        195                 200                 205

Gly Arg Arg Arg Val Ser Ile Val Pro Ser Ala Glu Gly Phe Gly Glu
    210                 215                 220

Ala Ile Arg Arg Gly Leu Gly Trp Gly Leu Leu Pro Glu Thr Gln Ala
225                 230                 235                 240

Ala Pro Met Leu Lys Ala Gly Glu Val Ile Leu Leu Asp Glu Ile Pro
                245                 250                 255

Ile Asp Thr Pro Met Tyr Trp Gln Arg Trp Arg Leu Glu Ser Arg Ser
            260                 265                 270
```

```
Leu Ala Arg Leu Thr Asp Ala Val Val Asp Ala Ala Ile Glu Gly Leu
        275                 280                 285
Arg Pro
    290
```

PROCESS FOR THE FERMENTATIVE PREPARATION OF L-ORNITHINE

CROSS-REFERENCE TO RELATED APPLICATION(S)

This application claims priority to DE 102010003419.3, filed Mar. 30, 2010 which is incorporated by reference in its entirety.

BACKGROUND OF THE INVENTION

1. Field of the Invention

A process for the fermentative preparation of L-ornithine and microorganisms characterized by an increased export of the amino acid.

2. Description of the Related Art

L-Ornithine is known for its stimulatory action regarding liver function and is frequently utilized as an ingredient of medicaments and in sports nutrition.

L-Ornithine is nowadays prepared by various processes. One method is the fermentative preparation with the aid of microorganisms. Another method is alkaline hydrolysis of arginine, for example with barium hydroxide (CN 1594282 A). Another method is the biotransformation of arginine by immobilized microorganisms possessing an arginase activity (KR589121B1). A method of preparing L-ornithine from L-citrulline has also been described in the patent literature (JP 42007767 B4).

Microorganisms which are distinguished in that they eliminate L-ornithine into the culture medium have been described in the literature. Examples of said microorganisms are bacteria of the genus *Corynebacterium, Brevibacterium, Bacillus* (JP 43010996 B4, JP 57041912 B), *Escherichia* (U.S. Pat. No. 3,668,072 A), *Providencia* (JP 03195494) or *Arthrobacter* (U.S. Pat. No. 3,574,061).

L-Ornithine-producing microorganisms are often distinguished by being auxotrophic for the amino acids L-arginine or L-citrulline (described for *Brevibacterium, Bacillus, Corynebacterium* in EP 392708 B1 and KR 161147 B1 and for *Escherichia* in U.S. Pat. No. 366,072 A). Furthermore, microorganisms have been described which are resistant to 2-thiazole-alanine, sulphaguanidine or 2-fluoropyruvate (Japanese Open-Laid publication No. 61-119194). EP 0393708 B1 describes L-ornithine producers which are distinguished by a lower resistance to ornithole and mycophenolic acid. Said properties may also be in a combined form.

The release of basic amino acids such as L-lysine, L-arginine and L-ornithine by way of passive diffusion from the cell is very poor (Bellmann et al. (Microbiology 2001; 147: 1765-74)). This has been well described for lysine by way of example. Vrlijc et al. (Journal of Bacteriology 1995; 177(14): 4021-7) have studied a plurality of export-deficient *Corynebacterium glutamicum* mutants. For one mutant, an intracellular concentration of 174 mM L-lysine was measured, while a value of only 0.7 mM was measured extracellularly.

Vrlijc et al. (Molecular Microbiology 1996; 22(5): 815-26 and Journal of Molecular Microbiology and Biotechnology 1999; 1: 327-336) and EP 0868527 B1 identified and described a novel exporter as L-lysine exporter (LysE). A defined LysE null mutant was no longer capable of transporting L-lysine out of the cell. The polypeptide encoded by the lysE gene is 233 amino acids or amino acid residues in length and is represented in SEQ ID No. 2. After overexpression of the lysE gene in a lysine producer, an increase in L-lysine elimination was found.

Von Bellmann et al. (Microbiology 2001; 147: 1765-74) have characterized in more detail the LysE exporter with regard to the transport of various basic amino acids in *C. glutamicum*. The authors demonstrated that the transporter specifically exports the amino acids L-lysine and L-arginine out of the cell. The authors furthermore investigated whether LysE also exports L-ornithine out of the cell. For this purpose, first of all an L-arginine-auxotrophic *C. glutamicum* strain referred to as ATCC13032::argF was prepared.

The strain was cultured in 50 ml (batch culture) of a minimal medium referred to as CGXII which contained 40 g/l glucose. After an incubation period of 24 hours 60 mM L-ornithine, corresponding to 7.9 g/l, were measured. Intracellularly, an L-ornithine concentration of approx. 200 mM was measured in the cells of said strain over an incubation period of approx. 70 minutes. In order to clarify, whether LysE also transports L-ornithine out of the cell, the strain 13032::argF was transformed with the replicative plasmid pEC7lysE. This measure was intended to provide the strain with an increased LysE activity, thereby allowing the strain to transport L-ornithine into the medium at a higher rate of export. However, said measure did not increase the rate of L-ornithine export. The same rate of export (0.6 nmol min$^{-1}$ (mg of dry mass)$^{-1}$) was determined both for the control strain (13032::argF) and in the transformant (13032::argF, harbouring pEC7lysE). From this the authors concluded that L-ornithine is not exported by the LysE exporter. They furthermore drew the conclusion that there must be another, unknown export function (export protein) for L-ornithine in *Corynebacterium glutamicum* (Bellmann et al., 2001, page 1771, FIG. 5b) and page 1772, lines 21-28).

A variant LysE (see SEQ ID No. 4) was identified in *C. glutamicum* R, which differs from the amino acid sequence of the LysE exporter from strain ATCC 13032, depicted in SEQ ID No. 2, by an N terminus extended by three amino acid residues. The sequence of said amino acid residues is: methionine, valine, isoleucine (MVI). This LysE polypeptide from strain R has been described in EP 1266966 B1 as a variant which differs from the wild-type protein in the formation of a loop region or, more specifically, can no longer form said loop, and is therefore able to accomplish improved export of L-lysine and L-arginine.

Another LysE variant has been described by Gunji and Yasueda (Journal of Biotechnology 127, 2006, 1-13). The authors were interested in L-lysine formation by the obligately methylotrophic bacterium, *Methylophilus methylotrophus*. They transformed *M. methylotrophus* with a plasmid referred to as pSE which contained the *C. glutamicum* ATCC13869 lysE gene in order to improve lysine formation by *M. methylotrophus*. However, the authors found that they were able to establish only a mutated form of the lysE gene (lysE24) in a stable manner in *M. methylotrophus*. The open reading frame of the lysE gene has been shifted in the lysE24 allele due to the insertion of a thymine residue, resulting in the termination of the reading frame after 432 bp. The truncated reading frame codes for a LysE protein which is shorter by 92 aa residues at the C terminus than the wild-type LysE protein of *C. glutamicum* ATCC13869. It is 141 amino acid residues in length. In addition, the last 6 C-terminal amino acids of the truncated protein (residues 135-141) differ from the amino acids of the wild-type LysE amino acid sequence. An *M. methylotrophus* strain carrying the modified LysE allele on a plasmid (pSE24) was tested for lysine formation. To this end, the strain was assayed in 0.3 l of a minimal medium referred to as SEIIc in the form of a fed-batch culture for 50 hours. The authors found that the transformant also formed small quantities (0.07 mM corresponding to 11.8 mg/l) of L-ornithine, in addition to 0.55 mM L-lysine and 0.19 mM L-arginine. As explained by the authors, this observed formation of L-ornithine is due to either an altered substrate specificity of the mutated transporter or possibly the altered intracellular L-arginine pool of the strain. EP 1266966 B1 (inventors: Gunji and Yasueda) describes the positive action of the LysE24 transporter on the elimination of L-lysine and L-arginine.

BRIEF SUMMARY OF THE INVENTION

The invention relates to a process for the preparation of L-ornithine, characterized in that the following steps are carried out:
a) fermentation of an L-ornithine-eliminating bacterium selected from the group consisting of *Corynebacterium, Bacillus, Streptomyces, Arthrobacter* and the Enterobacteriaceae which overexpresses a polynucleotide coding for a polypeptide which has the activity of an L-ornithine exporter and whose amino acid sequence is at least ($\geq$) 35%, $\geq$40%, $\geq$50%, $\geq$55%, $\geq$60%, $\geq$65%, $\geq$70%, $\geq$75%, $\geq$80%, $\geq$85%, $\geq$90%, $\geq$92%, $\geq$94%, $\geq$96%, $\geq$97%, $\geq$98%, $\geq$99% or 100%, preferably $\geq$70%, particularly preferably $\geq$90% or 95%, very particularly preferably $\geq$96%, and most preferably 100%, identical to the amino acid sequence of SEQ ID No. 2, in a medium,
b) accumulation of said L-ornithine in said medium, wherein a fermentation broth is obtained,
c) wherein the plasmid pEC7lysE, deposited in DSM23239, is not used for overexpression,
d) and wherein the length of the encoded polypeptide, where appropriate, is $\geq$146 to $\leq$286 of amino acids or amino acid residues.

Preference is given to selecting length ranges from the group consisting of $\geq$171 to $\leq$286, $\geq$196 to $\leq$261, $\geq$203 to $\leq$258, $\geq$218 to $\leq$243, $\geq$228 to $\leq$236, and $\geq$228 to $\leq$233 amino acids or amino acid residues.

Particular preference is given to the length ranges $\geq$203 to $\leq$258, $\geq$218 to $\leq$243, $\geq$228 to $\leq$236, and $\geq$228 to $\leq$233, and very particular preference is given to the length ranges $\geq$228 to $\leq$236 and $\geq$228 to $\leq$233.

Where L-ornithine is mentioned hereinbelow, the term also comprises its salts such as, for example, L-ornithine monohydrochloride or L-ornithine sulphate.

BRIEF DESCRIPTION OF THE DRAWINGS

FIGS. 1A-B depict a multiple sequence alignment of the amino acid sequences of the LysE polypeptides of the bacteria listed in Table 1. Alignment of the amino acid sequences of the LysE and Argo proteins listed in Table 1. Alignment gaps are indicated by "-". Identical amino acids are indicated by "*".

DETAILED DESCRIPTION OF THE INVENTION

Figure 2:
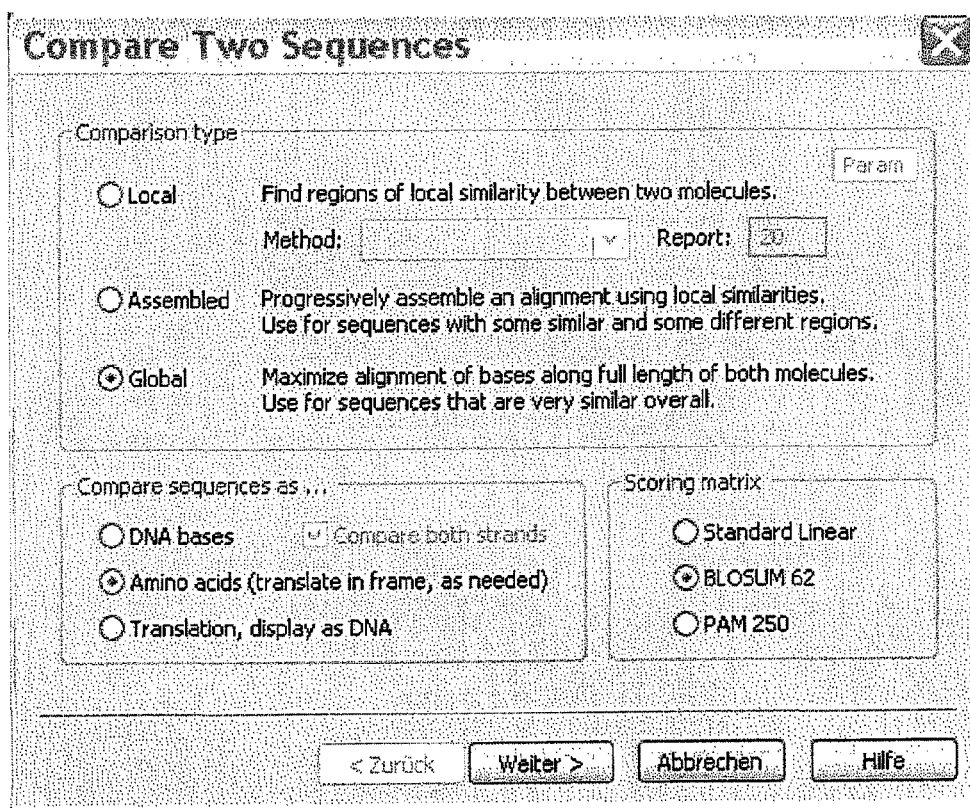
FIG. 2 shows the setting of the Clone Manager 9 program (Scientific and Educational Software) for determining the identity of two amino acid sequences by global sequence alignment.

A process according to the invention makes use of bacteria selected from the group consisting of the genera *Corynebacterium, Bacillus, Streptomyces, Arthrobacter* and the Enterobacteriaceae family.

Within the genus *Corynebacterium*, preference is given to strains based on the following species:

*Corynebacterium efficiens*, for example the type strain DSM44549,
*Corynebacterium glutamicum*, for example the type strain ATCC13032 or the strain R, and
*Corynebacterium ammoniagenes*, for example the strain ATCC6871,
with very particular preference being given to the species *Corynebacterium glutamicum*.

Some representatives of the species *Corynebacterium glutamicum* are also known in the prior art under other names. These include for example:
strain ATCC13870, referred to as *Corynebacterium acetoacidophilum*,
strain DSM20137, referred to as *Corynebacterium lilium*,
strain ATCC17965, referred to as *Corynebacterium melassecola*,
strain ATCC14067, referred to as *Brevibacterium flavum*,
strain ATCC13869, referred to as *Brevibacterium lactofermentum*, and
strain ATCC14020, referred to as *Brevibacterium divaricatum*.

The term "*Micrococcus glutamicus*" for *Corynebacterium glutamicum* has likewise been in use. Some representatives of the species *Corynebacterium efficiens* have also been referred to in the prior art as *Corynebacterium thermoaminogenes*, for example the strain FERM BP-1539.

Within the genus *Bacillus*, preference is given to the species *Bacillus subtilis*.

Within the genus *Arthrobacter*, preference is given to the species *Arthrobacter citreus*.

Within the Enterobacteriacae family, preference is given to the genera *Escherichia, Erwinia, Providencia, Pantoea* and *Serratia*. Particular preference is given to the genera *Escherichia* and *Serratia*. Very particular preference is given to the species *Escherichia coli* in the genus *Escherichia*, to the species *Serratia marcescens* in the genus *Serratia*, and to the species *Providencia rettgeri* in the genus *Providencia*.

The bacteria or strains (starting strains) employed for the measures of overexpressing the L-ornithine exporter preferably already have the ability to eliminate L-ornithine into the nutrient medium surrounding them and accumulate it there. The expression "to produce" is also used for this hereinbelow. More specifically, the strains employed for said overexpression measures have the ability to concentrate or accumulate in the nutrient medium $\geq$0.1 g/l, $\geq$0.3 g/l, $\geq$1 g/l, $\geq$3 g/l, $\geq$10 g/l L-ornithine. The starting strains are preferably strains which have been prepared by mutagenesis and selection, by recombinant DNA technologies or by a combination of both methods.

A bacterium suitable for the measures of the invention may also be obtained by firstly overexpressing a polynucleotide coding for a polypeptide which has the activity of an L-ornithine exporter and whose amino acid sequence is at least ($\geq$) 35% identical to that of SEQ ID No. 2, with the length of the encoded polypeptides, where appropriate, being within the length ranges described above, in a wild strain such as, for example, in the *Corynebacterium glutamicum* type strain ATCC 13032 or in the strain ATCC 14067, and subsequently causing said bacterium, by further genetic measures described in the prior art, to produce L-ornithine. Transforming a wild type, such as e.g. the strain ATCC13032, ATCC14067, ATCC13869 or ATCC17965, only with the polynucleotide mentioned does not result in a process according to the invention.

Examples of strains of the species *Corynebacterium glutamicum* which eliminate or produce L-ornithine are:

*Brevibacterium lactofermentum* FERM-BP 2344, and *Corynebacterium glutamicum* FERM-BP 2345 described in U.S. Pat. No. 5,188,947.

An example of a strain of the species *Arthrobacter citreus* which eliminates or produces L-ornithine is:

*Arthrobacter citreus* FERM-BP 2342 described in U.S. Pat. No. 5,188,947.

An example of a strain of the species *Bacillus subtilis* which eliminates or produces L-ornithine is:

*Bacillus subtilis* BOR-32 (FERM-P 3647) described in JP 57041912.

An example of a strain of the species *Providencia rettgeri* which eliminates or produces L-ornithine is:

*Providencia rettgeri* ARGA6 (FERM P-11147) described in JP 03195494.

An example of a strain of the species *Escherichia coli* which eliminates or produces L-ornithine is:

*Escherichia coli* B-19-19 (ATCC 21104) described in U.S. Pat. No. 3,668,072.

L-Ornithine-producing bacteria typically are auxotrophic for the amino acids L-citrulline or L-arginine. As an alternative, L-orthinine-producing bacteria which are bradytrophic for L-citrulline or L-arginine may also be contemplated. Definitions of the terms auxotrophic and bradytrophic can be found, for example, on page 9 of WO 01/09286. Bradytrophs are also referred to as leaky mutants in the art. Bradytrophic bacteria used are in particular those in which the activity of the gene products ArgF (ornithine carbamoyl transferase), ArgG (argininosuccinate synthase) or ArgH (argininosuccinate lyase) is greater than (>) zero but equal to or less than (≤) 10 percent, preferably >zero and ≤1%, compared to the activity in the wild type.

The prior art has disclosed polynucleotides which are referred to as lysE gene and which code for proteins or polypeptides having the activity of an L-lysine exporter. These polypeptides are also referred to by the abbreviation LysE.

An exporter is a protein which resides in the cell membrane of a cell and which transports a metabolite, for example L-lysine or L-ornithine, from the cytoplasma of said cell out into the surrounding medium. If the energy required for this is provided in the form of adenosine triphosphate (ATP), this is referred to as primary active transport or export. It is referred to as secondary active transport or export if said energy is provided in the form of an ion gradient, for example of sodium ions (Jeremy M. Berg, John L. Tymoczko and L. Stryer; Biochemie [Biochemistry], 5$^{th}$ edition, pages 378-384, Spektrum Akademischer Verlag [publisher], Heidelberg, Germany, 2003). Instructions for determining L-ornithine export activity can be found in Bellmann et al. (Microbiology 2001; 147: 1765-74).

In the course of the work leading to the present invention the lysine exporters of the genera *Corynebacterium*, preferably *Corynebacterium glutamicum*, and *Micrococcus*, preferably *Micrococcus luteus*, were found to have the activity of an L-ornithine exporter in addition to the L-lysine export activity.

The measures of the invention make use of genes coding for polypeptides which have export activity for L-ornithine and whose amino acid sequence is at least (≥) 35%, ≥40%, 50%, ≥55%, ≥60%, ≥65%, ≥70%, ≥75%, ≥80%, ≥85%, ≥90%, ≥92%, ≥94%, ≥96%, ≥97%, ≥98%, ≥99% or 100%, preferably ≥70%, particularly preferably 90%, very particularly preferably ≥96%, and most preferably ≥100%, identical to the amino acid sequence of SEQ ID No. 2, with the length of the encoded polypeptide, where appropriate, being within the above-described length ranges.

Examples of suitable L-ornithine exporters are the lysine exporters or LysE polypeptides of *Corynebacterium glutamicum* ATCC13032 (SEQ ID No. 2), *Corynebacterium glutamicum* R (SEQ ID No. 4), *Corynebacterium glutamicum* ATCC14067 (SEQ ID No. 5), *Corynebacterium glutamicum* ATCC13869 (SEQ ID No. 7), *Corynebacterium efficiens* YS-314 (SEQ ID No. 9), *Corynebacterium diphteriae* NCTC 13129 (SEQ ID No. 10), *Corynebacterium striatum* ATCC6940 (SEQ ID No. 11), *Corynebacterium aurimucosum* ATCC700975 (SEQ ID No. 12), *Corynebacterium matruchotii* ATCC33806 (SEQ ID No. 13), *Corynebacterium pseudogenitalium* ATCC33035 (SEQ ID No. 14), *Corynebacterium accolens* ATCC49725 (SEQ ID No. 15), *Corynebacterium glucuronalyticum* ATCC 51867 (SEQ ID No. 16), *Micrococcus luteus* NCTC2665 (SEQ ID No. 17), *Corynebacterium tubuculostearicum* SK141 (SEQ ID No. 18) and *Corynebacterium matruchotii* ATCC14266 (SEQ ID No. 19). SEQ ID No. 18 and SEQ ID No. 19 are also referred to as Argo polypeptides in the art.

The nucleotide sequence of the lysE genes of *Corynebacterium glutamicum* ATCC14067 and *Corynebacterium glutamicum* ATCC13869 was determined in this study (SEQ ID No. 6 and SEQ ID No. 8). The amino acid sequences of the LysE polypeptide of *Corynebacterium glutamicum* ATCC14067 and *Corynebacterium glutamicum* ATCC13869 are depicted in SEQ ID No. 5 and 7. They are identical to the amino acid sequence of *C. glutamicum* ATCC13032 LysE, depicted in SEQ ID No. 2.

Table 1 lists the accession numbers of LysE polypeptides of various representatives of the genus *Corynebacterium* and of *Micrococcus luteus*, which were taken from the databases of the National Center for Biotechnology Information (NCBI, Bethesda, Md., US). Furthermore, Table 1 makes reference to the amino acid sequences of the LysE polypeptide that are depicted in the sequence listing. Finally, Table 1 indicates the length (number of amino acids) of the encoded LysE polypeptide.

TABLE 1

| Bacterium | SEQ ID No. | Accession number | Length of polypeptide |
|---|---|---|---|
| C. glutamicum | 2 | YP_225551.1 | 233 |
| C. efficiens | 9 | ZP_05749209.1 | 228 |
| C. diphteriae | 10 | NP_939452.1 | 228 |
| C. striatum | 11 | ZP_03933958.1 | 222 |
| C. aurimucosum | 12 | YP_002834652.1 | 235 |
| C. matruchotii | 13 | ZP_03711883.1 | 244 |
| C. pseudogenitalium | 14 | ZP_03922319.1 | 230 |
| C. accolens | 15 | ZP_03931790.1 | 241 |
| C. glucuronolyticum | 16 | ZP_03918361.1 | 261 |
| M. luteus | 17 | YP_002958101.1 | 204 |
| C. tubuculostearicum | 18 | ZP_05365683.1 | 230 |
| C. matruchotii | 19 | ZP_04835056.1 | 244 |

FIG. 1 depicts a multiple sequence alignment of the amino acid sequences of the LysE polypeptides of the bacteria listed in Table 1. SEQ ID No: 2 (YP 225551.1); SEQ ID No:9 (ZP 05749209.1); SEQ ID No:10 (NP 939452.1); SEQ ID No:11 (ZP 03933958.1); SEQ ID No:12 (YP 002834652.1); SEQ ID No:13 (ZP 03711883.1); SEQ ID No:14 (ZP 03922319.1); SEQ ID No:15 (ZP 03931790.1); SEQ ID No:16 (ZP 03918361.1); SEQ ID No:17 (YP 002958101.1); SEQ ID No:18 (ZP 05365683.1); SEQ ID No:19 (ZP 04835056.1). The alignments of the amino acid sequences depicted in FIG. 1 were produced by the program Clone Manager 9 Professional Edition (Scientific & Educational Software 600 Pinner Weald Way Ste 202 Cary N.C. 27513 USA). The reference molecule used for the alignment was the LysE polypeptide (LysE) of ATCC13032. For the scoring matrix, the setting "Blosum 62" (see: Jeremy M. Berg, John L. Tymoczko and L. Stryer; Biochemie, 5$^{th}$ edition, pages 194-197, Spektrum Akademischer Verlag, Heidelberg, Germany, 2003)) was chosen.

It is also possible, where appropriate, to employ programs described in the prior art, such as, for example, the ClustalX program (Thompson, J. D., Gibson, T. J., Plewniak, F., Jeanmougin, F. and Higgins, D. G. (1997). The ClustalX windows interface: flexible strategies for multiple sequence alignment aided by quality analysis tools. Nucleic Acids Research, 25: 4876-4882).

The amino acid residues 4-236 of the LysE polypeptide of *Corynebacterium glutamicum* R (see SEQ ID No. 4) correspond to the *C. glutamicum* ATCC13032 LysE amino acid sequence depicted in SEQ ID No. 2. The *C. glutamicum* R polypeptide has N-terminally an additional sequence of three amino acid residues (methionine-valine-isoleucine). These additional residues are produced when the start codon located 9 base pairs further upstream of the lysE gene is used as an alternative to the start codon of the lysE gene in *C. glutamicum* ATCC13032 (see SEQ ID No. 1).

The amino acid sequence of the LysE polypeptide of *C. efficiens* YS-314 is 71%, and that of *C. diphteriae* NCTC 13129 is 44%, that of *Corynebacterium striatum* ATCC6940 is 44%, that of *Corynebacterium aurimucosum* ATCC700975 is 42%, that of *Corynebacterium matruchotii* ATCC33806 is 43%, that of *Corynebacterium pseudogenitalium* ATCC33035 is 43%, that of *Corynebacterium accolens* ATCC49725 is 43%, that of *Corynebacterium glucuronalyticum* ATCC 51867 is 36%, that of *Micrococcus luteus* NCTC2665 is 40%, identical to the *C. glutamicum* ATCC13032 LysE amino acid sequence depicted in SEQ ID No. 2. Furthermore, the amino acid sequence of the ArgO polypeptide of *C. tubuculostearicum* SK141 is 43% identical to the amino acid sequence of SEQ ID No. 2. Furthermore, the amino acid sequence of the Argo polypeptide of *C. matruchotii* ATCC14266 is 44% identical to the amino acid sequence of SEQ ID No. 2. The identity percentages were produced by generating a global sequence alignment with the aid of the Clone Manager 9 program using the Blosum 62 setting (see FIG. 2).

The lysE genes, i.e. the polynucleotides coding for polypeptides having the activity of an L-ornithine exporter, may be isolated from the organisms with the aid of the polymerase chain reaction (PCR) using suitable primers. Instructions can be found inter alia in the laboratory manual "PCR" by Newton and Graham (Spektrum Akademischer Verlag, Heidelberg, Germany, 1994), and in WO 2006/100211 on pages 14 to 17.

Particular preference is given to employing for a process according to the invention genes coding for polypeptides which have L-ornithine export activity and whose amino acid sequence includes one or more of the features selected from the group consisting of a) amino acid sequence according to SEQ ID No. 2 or SEQ ID No. 4,
b) amino acid sequence according to SEQ ID No. 2, including one or more, up to 25, 20, 15, 10, 5, 4, 3, 2, or 1, deletion(s) of amino acids,
c) amino acid sequence according to SEQ ID No. 2, including one or more, up to 25, 20, 15, 10, 5, 4, 3, 2, or 1, insertion (s) of amino acids, and
d) amino acid sequence according to SEQ ID No. 2, including one or more, up to 140, 130, 120, 110, 100, 90, 80, 70, 60, 50, 40, 30, 25, 20, 15, 10, 5, 4, 3, 2, or 1, preferably up to 5, 4, 3, 2, or 1, replacement(s) (substitution(s)) of amino acids.
e) amino acid sequence according to SEQ ID No. 2, including one or more, up to 25, 20, 15, 10, 5, 4, 3, 2, or 1, preferably up to 5, 4, 3, 2, or 1, addition(s) of amino acids on the N terminus and/or on the C terminus.

Where appropriate, preference is given to conservative amino acid substitutions. In the case of aromatic amino acids, conservative substitutions are those in which phenylalanine, tryptophan and tyrosine are substituted for each other. In the case of hydrophobic amino acids, conservative substitutions are those in which leucine, isoleucine and valine are substituted for one another. In the case of polar amino acids, conservative substitutions are those in which glutamine and asparagine are substituted for one another. In the case of basic amino acids, conservative substitutions are those in which arginine, lysine and histidine are substituted for one another. In the case of acidic amino acids, conservative substitutions are those in which aspartic acid and glutamic acid are substituted for one another. In the case of amino acids containing hydroxyl groups, conservative substitutions are those in which serine and threonine are substituted for one another.

It is furthermore possible to use polynucleotides which hybridize under stringent conditions with the nucleotide sequence complementary to SEQ ID No. 1, preferably to the coding region of SEQ ID No. 1, and code for a polypeptide having L-ornithine export activity, with the amino acid sequence of the encoded protein being ≥70% identical to the amino acid sequence of SEQ ID No. 2 and the length of the encoded polypeptide, where appropriate, being within the above-described length ranges.

Instructions regarding the hybridization of nucleic acids and polynucleotides, respectively, can be found by the skilled worker inter alia in the manual "The DIG System Users Guide for Filter Hybridization" from Boehringer Mannheim GmbH (Mannheim, Germany, 1993) and in Liebl et al. (International Journal of Systematic Bacteriology 41: 255-260 (1991)). Hybridization takes place under stringent conditions, that is to say only hybrids are formed in which the probe, i.e. a polynucleotide comprising the nucleotide sequence complementary to SEQ ID No. 1, preferably the coding region of SEQ ID No. 1, and the target sequence, i.e. the polynucleotides treated with or identified by said probe, are at least 70%, 80%, 90%, 95% or 99% identical. The stringency of the hybridization, including the washing steps, is known to be influenced or determined by varying the buffer composition, temperature and salt concentration. The hybridization reaction is generally carried out with relatively low stringency compared with the washing steps (Hybaid Hybridisation Guide, Hybaid Limited, Teddington, UK, 1996).

For example, a 5×SSC buffer at a temperature of approx. 50° C.-68° C. may be employed for the hybridization reaction. Here, probes can also hybridize with polynucleotides which are less than 70% identical to the nucleotide sequence of the probe employed. Such hybrids are less stable and are removed by washing under stringent conditions. This may be achieved, for example, by lowering the salt concentration to 2×SSC or 1×SSC and, where appropriate, subsequently 0.5× SSC (The DIG System User's Guide for Filter Hybridisation, Boehringer Mannheim, Mannheim, Germany, 1995), with a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being set. Preference is given to temperature ranges of approx. 64° C.-68° C. or approx. 66° C.-68° C. It is optionally possible to lower the salt concentration to a concentration corresponding to 0.2× SSC or 0.1×SSC. The SSC buffer optionally contains sodium dodecyl sulphate (SDS) at a concentration of 0.1%. By gradually increasing the hybridization temperature in steps of approx. 1-2° C. from 50° C. to 68° C., it is possible to isolate polynucleotide fragments which are at least 70%, at least 80%, at least 90%, at least 92%, at least 94%, at least 95%, at least 96%, at least 97%, at least 98%, or at least 99%, where appropriate 100%, identical to the sequence or complementary sequence of the probe employed and which code for a polypeptide having L-ornithine export activity. Further instructions regarding hybridization are obtainable on the market in the form of "kits" (e.g. DIG Easy Hyb from Roche Diagnostics GmbH, Mannheim, Germany, Catalogue No. 1603558).

For the measures of the invention, a polynucleotide coding for a protein which has L-ornithine export activity is overexpressed in a bacterium or starting or parent strain producing L-ornithine, with the amino acid sequence of the encoded protein being ≥35% identical to the amino acid sequence of SEQ ID No. 2 and the length of the encoded polypeptide, where appropriate, being within the above-described ranges.

Overexpression generally means an increase in the intracellular concentration or activity of a ribonucleic acid, of a protein (polypeptide) or of an enzyme by comparison with the starting strain (parent strain) or wild-type strain, if the latter is the starting strain. A starting strain (parent strain) means the strain on which the measure leading to overexpression has been carried out.

The terms protein and polypeptide are considered to be interchangeable.

For overexpression, preference is given to the methods of recombinant overexpression. These include any methods in which a microorganism is prepared using a DNA molecule provided in vitro. Examples of such DNA molecules include promoters, expression cassettes, genes, alleles, coding regions, etc. They are transferred by methods of transformation, conjugation, transduction or similar methods into the desired microorganism.

The measures of overexpression increase the activity or concentration of the corresponding polypeptide generally by at least 10%, 25%, 50%, 75%, 100%, 150%, 200%, 300%, 400% or 500%, preferably by up to 1000%, 2000%, 4000%, 10 000% or 20 000%, based on the level of activity or concentration of said polypeptide in the strain prior to the measure resulting in overexpression.

When using strains of the species Corynebacterium glutamicum, the L-ornithine export activity in strain ATCC13032 or ATCC14067 or ATCC13869 or ATCC17965, where appropriate, is a suitable reference point for determining overexpression. When using strains based on or derived from ATCC13032, said strain ATCC13032 is a suitable reference point. An example of this is the strain prepared in the course of the work leading to the present invention, ATCC13032_Delta_argFRGH/pVWEx1_lysE, which is based on the strain ATCC13032. When using strains based on or derived from ATCC14067, said strain ATCC14067 is a suitable reference point. When using strains based on or derived from ATCC13869, said strain ATCC13869 is a suitable reference point. Further suitable reference points are produced accordingly.

When using strains of the species Escherichia coli, preferably Escherichia coli strain K12, the L-ornithine export activity in strain MG1655, where appropriate, is a suitable reference point for determining overexpression.

Overexpression is achieved by a multiplicity of methods available in the prior art.

These include increasing the copy number and modifying the nucleotide sequences directing or controlling expression of the gene. Transcription of a gene is controlled inter alia by the promoter and optionally by proteins which suppress (repressor proteins) or promote (activator proteins) transcription. Translation of the RNA formed is controlled inter alia by the ribosome binding site and the start codon. Polynucleotides or DNA molecules which include a promoter and a ribosome binding site and optionally a start codon are also referred to as expression cassette.

Said methods also include the use of variants of polypeptides or enzymes, which have an increased catalytic activity.

The copy number may be increased by means of plasmids which replicate in the bacterial cytoplasm. To this end, an abundance of plasmids are described in the prior art for very different groups of microorganisms, which plasmids can be used for setting the desired increase in the copy number of the gene. Plasmids suitable for the genus Escherichia are described, for example, in the manual Molecular Biology, Labfax (Ed.: T. A. Brown, Bios Scientific, Oxford, UK, 1991). Plasmids suitable for the genus Corynebacterium are described, for example, in Tauch et al. (Journal of Biotechnology 104 (1-3), 27-40, (2003)) or in Stansen et al. (Applied and Environmental Microbiology 71, 5920-5928 (2005)).

The use of plasmid pEC7lysE, deposited in DSM 23239, for increasing the copy number in Corynebacterium glutamicum strains is excluded from the measures leading to the present invention. The nucleotide sequence of the pEC7lysE plasmid was determined and is depicted in SEQ ID No. 29.

The copy number may furthermore be increased by at least one (1) copy by introducing further copies into the bacterium chromosome. Methods suitable for the genus Corynebacterium, preferably Corynebacterium glutamicum, are described, for example, in the patents WO 03/014330, WO 03/040373 and WO 04/069996. WO 03/014330 describes methods for tandem doubling of genes at the native gene locus. WO 03/040373 describes methods for incorporating a second or third copy of a gene at further gene loci, with the particular gene locus being non-essential for growth or production of the particular amino acid, L-ornithine in the case of the present invention. Examples of suitable gene loci for incorporating a second or further copy of the lysE gene in a process according to the invention are the genes odh, sucA, dapA, dapB, ddh, lysA, argR, argF, argG and argH. WO 04/069996 (see Tables 12 and 13) describes C. glutamicum intergenic regions and genes coding for phages or phage components, which are suitable for incorporating further copies of the lysE gene.

Examples of methods suitable for the genus Escherichia are incorporation of a gene copy into the att site of the phage (Yu and Court, Gene 223, 77-81 (1998)), chromosomal amplification with the aid of the phage Mu, as described in EP 0 332 448, or the methods of gene replacement with the aid of conditionally replicating plasmids, as described by Hamilton et al. (Journal of Bacteriology 174, 4617-4622 (1989)) or Link et al. (Journal of Bacteriology 179, 6228-6237 (1997)).

Gene expression may furthermore be increased by using a strong promoter which is functionally linked to the gene to be expressed. Preference is given to using a promoter which is stronger than the natural promoter, i.e. the one present in the wild type or parent strain. To this end, the prior art has an abundance of methods available.

Suitable promoters and expression systems for the genus Corynebacterium can be found inter alia in the patents EP 0 629 699 A2, US 2007/0259408 A1 (gap promoter), WO 2006/069711, EP 1 881 076 A1, WO 2008/088158, WO 2009/

025470 (butA promoter, pyk promoter), U.S. Pat. No. 6,861, 246 (MC20 and MA16 variants of the dapA promoter), and EP 1 918 378 A1 (sod promoter), and in overviews such as the "Handbook of *Corynebacterium glutamicum*" (Eds.: Lothar Eggeling and Michael Bott, CRC Press, Boca Raton, US (2005)), or the book "Corynebacteria, Genomics and Molecular Biology" (Ed.: Andreas Burkovski, Caister Academic Press, Norfolk, UK (2008)). Examples of promoters which allow controlled, i.e. inducible or repressible, expression are described, for example, in Tsuchiya and Morinaga (Bio/Technology 6, 428-430 (1988)).

Promoters suitable for the genus *Escherichia* have been known for a long time. They include, inter alia, the classical promoters lac promoter, trp promoter, the hybrid promoters tac and trc, the PL and PR promoters of phage λ. Similarly, it is possible to use the promoters of the T7 phage, the gear-box promoters, the nar promoter or the promoters of the genes rrsG, rnpB, csrA, csrB, ompA, fusA, pepQ, rplX or rpsG. Controlled expression is permitted, for example, by the cI857-PR or the cI857-PL system of the λ phage (Götting et al., BioTechniques 24, 362-366 (1998)). Overviews can be found in Makrides (Microbiological Reviews 60(3), 512-538 (1996)) or in the manual "*Escherichia coli* and *Salmonella*, Cellular and Molecular Biology" (F. C. Neidhardt (Editor in Chief), ASM Press, Washington, US (1996)).

Such promoters or expression cassettes are typically employed at a distance of from 1 to 1000, preferably 1 to 500, nucleotides upstream of the first nucleotide of the start codon of the coding region of the gene. At a distance of 1 means that the promoter or the expression cassette is positioned immediately in front of the first base of the start codon of the coding region.

To increase expression of the lysE gene in *C. glutamicum*, preference is given to inserting suitable promoters such as, for example, the *C. glutamicum* sod promoter (see SEQ ID No. 1 of EP 1918 378 A1) or the *C. glutamicum* gap promoter (see SEQ ID No. 3 of US 2007/0259408) between positions 930 and 990 of SEQ ID No. 1.

When using expression cassettes containing a promoter and a ribosome binding site (RBS), such as the expression unit of the *C. glutamicum* sod gene (see SEQ ID No. 2 of EP 1918 378 A1) or the expression unit of the *C. glutamicum* gap gene, described in US 2007/0259408 and depicted in SEQ ID No. 28 (and referred to there as PgapRBS), for example, they are inserted, in the case of *C. glutamicum*, preferably between positions 930 and 1001, particularly preferably between positions 1000 and 1001, of SEQ ID No. 1. An example of a suitable ribosome binding site in such an expression cassette is the nucleotide sequence 5'-agaaaggagg-3' specified by Amador (Microbiology 145, 915-924 (1999)).

It is likewise possible to place a plurality of promoters upstream of the desired gene or functionally link them to the gene to be expressed and in this way achieve increased expression. This is described, for example, in WO 2006/069711.

The structure of *Corynebacterium glutamicum* and *Escherichia coli* promoters is well known. It is therefore possible to increase the strength of a promoter by modifying its sequence by means of one or more substitution(s) and/or one or more insertion(s) and/or one or more deletion(s) of nucleotides. Examples of this can be found inter alia in "Herder Lexikon der Biologie" [Herder's Encyclopaedia of Biology] (Spektrum Akademischer Verlag, Heidelberg, Germany (1994)).

Accordingly, a suitable measure for overexpressing the lysE gene is to modify or mutate the promoter of said lysE gene.

The structure of the *Corynebacterium glutamicum* and *Escherichia coli* ribosome binding sites is likewise well known and is described, for example, in Amador (Microbiology 145, 915-924 (1999)), and in manuals and text books of genetics, for example "Gene and Klone" [Genes and Clones] (Winnacker, Verlag Chemie, Weinheim, Germany (1990)) or "Molecular Genetics of Bacteria" (Dale and Park, Wiley and Sons Ltd., Chichester, UK (2004)). Well expressed genes, i.e. the most important structural genes in an organism, have a good ribosome binding site (Amador, Microbiology 145, 915-924 (1999)), i.e. the latter is very similar to or corresponds to the consensus sequence. It has been demonstrated in the literature that highly expressed genes have a strong ribosome binding site (Karlin and Mrázek, Journal of Bacteriology 2000; 182(18): 5238-50). Consequently, translation efficiency of a gene or of the mRNA can be achieved by adjusting the ribosome binding site.

It is also possible to increase translation efficiency by adjusting the codon usage in the genes to be expressed (e.g. Najafabiad et al., Nucleic Acids Research 2009, 37 (21): 7014-7023).

Overexpression can likewise be achieved by increasing the expression of activator proteins or by reducing or switching off the expression of repressor proteins.

The activator protein LysG for expressing lysE has been described by Bellmann et al. (Microbiology 2001; 147: 1765-74) and is referred to there as "positive regulator". The amino acid sequence of *Corynebacterium glutamicum* ATCC13032 LysG is depicted in SEQ ID No. 30. In a global sequence alignment, the amino acid sequence of the LysG polypeptide of *Corynebacterium diphteriae* NCTC13129 is 62%, the amino acid sequence of the LysG polypeptide of *Corynebacterium efficiens* YS-314 is 81%, and the amino acid sequence of the LysG polypeptide of *Corynebacterium glutamicum* R is 94%, identical to that of SEQ ID No. 30.

For activator proteins, preference is given to a polypeptide which is ≥ (at least) 55%, preferably ≥80%, particularly preferably ≥90%, ≥92% or ≥94%, very particularly preferably ≥99%, and most preferably 100%, identical to the amino acid sequence depicted in SEQ ID No. 30.

The overexpression measures mentioned, preferably selected from the group consisting of increasing the copy number, using a strong promoter, mutating the promoter, using a suitable expression cassette and overexpressing an activator protein, may be combined in a suitable manner. Thus it is possible, for example, to combine using a suitable promoter with increasing the copy number, or overexpressing an activator protein with using a suitable promoter or a suitable expression cassette.

It is likewise possible, in addition to the measures relating to the polynucleotide coding for a protein having L-ornithine export activity, to attenuate individual biosynthesis genes.

To improve production of L-ornithine, it is thus convenient, where appropriate, to attenuate additionally one or more of the genes selected from the group consisting of a) odhA gene coding for the E1 subunit of alpha-ketoglutarate dehydrogenase (EC 1.2.4.2),
b) sucA gene coding for dihydrolipoamide succinyl transferase (EC 2.3.1.61),
c) dapA gene coding for a dihydrodipicolinate synthase (DapA, EC 4.2.1.52),
d) dapB gene coding for a dihydrodipicolinate synthase (DapB, EC 1.3.1.26),
e) ddh gene coding for a meso-diaminopimelate dehydrogenase (Ddh, EC 1.4.1.16),
f) lysA gene coding for a diaminopimelate decarboxylase (LysA, EC 4.1.1.20), g) argR gene coding for a/the repressor (ArgR) of L-arginine biosynthesis,
h) argF gene coding for an ornithine carbamoyl transferase (ArgF, EC 2.1.3.3),
i) argG gene coding for an argininosuccinate synthase (ArgG, EC 6.3.4.5),
j) argH gene coding for an argininosuccinate lyase (ASAL) (ArgH, EC 4.3.2.1),
k) lysC gene coding for an aspartate kinase (LysC, EC 2.7.2.4), and
l) asd gene coding for an aspartate semialdehyde dehydrogenase (Asd, EC 1.2.1.11).

Preference is given to attenuating one or more of the genes selected from the group consisting of lysA, odhA, argR, argF, argG and argH. Particular preference is given to attenuating one or more of the genes selected from the group consisting of lysA, odhA and argF. Very particular preference is given to attenuating the genes lysA and/or argF.

The term "attenuation" in this context describes reducing or switching off the intracellular activity of one or more enzymes (proteins) in a bacterium, that are encoded by the corresponding DNA, by using, for example, a weak promoter or a gene or allele that codes for a corresponding enzyme having a low activity, or by inactivating the corresponding gene or enzyme (protein), and optionally combining these measures.

An overview of known promoters of various strengths in *Corynebacterium glutamicum* can be found in Pátek et al. (Journal of Biotechnology 104, 311-323 (2003)). Other weak promoters are described in the communication 512057 in the journal Research Disclosure from December 2006 (pages 1616 to 1618).

Mutations which may be considered for generating an attenuation are transitions, transversions, insertions and deletions of at least one (1) base pair or nucleotide in the coding region of the gene in question. Depending on the effect of the amino acid substitution caused by the mutation on the activity of the protein or enzyme, the mutations are referred to as missense mutations or nonsense mutations.

The missense mutation results in a replacement of a given amino acid in a protein with another one, said replacement being in particular a non-conservative amino acid substitution. This impairs the functionality or activity of the protein and reduces it to a value of from ≥0 to 75%, ≥0 to 50%, ≥0 to 25%, ≥0 to 10% or ≥0 to 5%.

The nonsense mutation results in a stop codon in the coding region of the gene and therefore in an early termination of translation and consequently to a switching-off. Insertions or deletions of at least one base pair in a gene lead to frame shift mutations resulting in wrong amino acids being incorporated or translation being terminated early. If the mutation results in a stop codon in the coding region, this likewise leads to an early termination of translation. The measures of generating a nonsense mutation are preferably carried out in the 5'-terminal part of the coding region, which codes for the N terminus of the polypeptide. If the overall length of a polypeptide (measured by way of the number of chemically linked L-amino acids) is referred to as 100%, then—within the scope of the present invention—the N terminus of the polypeptide includes that part of the amino acid sequence which, by calculation from the start amino acid, L-formyl-methionine, onwards, contains 801 of the downstream L-amino acids.

In-vivo mutagenesis methods are described, for example, in the Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)).

Suitable methods of in-vitro mutagenesis are, inter alia, the treatment with hydroxylamine according to Miller (Miller, J. H.: A Short Course in Bacterial Genetics. A Laboratory Manual and Handbook for *Escherichia coli* and OxyRated Bacteria, Cold Spring Harbor Laboratory Press, Cold Spring Harbor, 1992), the use of mutagenic oligonucleotides (T. A. Brown: Gentechnologie air Einsteiger [Genetic Engineering for Beginners], Spektrum Akademischer Verlag, Heidelberg, 1993 and R. M. Horton: PCR-Mediated Recombination and Mutagenesis, Molecular Biotechnology 3, 93-99 (1995)), and the use of a polymerase chain reaction using a DNA polymerase with a high error rate. An example of such a DNA polymerase is the Mutazyme DNA polymerase (GeneMorph PCR Mutagenesis Kit, No. 600550) from Stratagene (LaJolla, Calif., USA).

Further instructions and overviews on the generation of mutations in vivo or in vitro can be found in the prior art and in known text books of genetics and molecular biology, such as the text book by Knippers ("Molekulare Genetik", 6$^{th}$ edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik" [General Genetics], Gustav Fischer Verlag, Stuttgart, 1986), for example.

With the aid of the known process of gene or allele replacement, the fundamentals of which are described in Schwarzer and Püthier (Bio/Technology 9, 84-87 (1991)), it is possible to transfer a mutation prepared in vitro, or a polynucleotide containing the desired mutation, into the chromosome. Von Schafer et al. (Gene 145, 69-73 (1994)) employed this method in order to incorporate a deletion into the *C. glutamicum* hom-thrB operon. Von Nakagawa et al. (EP 1108790) and Ohnishi et al. (Applied Microbiology and Biotechnology 58(2), 217-223 (2002)) employed this method in order to incorporate various mutations, starting from the isolated alleles, into the *C. glutamicum* chromosome.

One method for targeted reduction of gene expression consists of placing the gene to be attenuated under the control of a promoter which can be induced by addition of metered amounts of IPTG (isopropyl β-D-thiogalactopyrano-side), such as, for example, the trc promoter or the tac promoter. Suitable for this purpose are vectors such as, for example, the *Escherichia coli* expression vector pXK99E (WO 0226787; deposited in accordance with the Budapest Treaty on 31$^{st}$ July 2001 in DH5alpha/pXK99E as DSM14440 with the Deutsche Sammlung für Mikroorganismen und Zellkulturen (DSMZ, Brunswick, Germany)), pEKEx2 (NCBI Accession No. AY585307) or pVWEx2 (Wendisch, Ph. D. thesis, Berichte des Forschungszentrums Jülich, Jül-3397, ISSN 0994-2952, Jülich, Germany (1997)), which enable the cloned gene to be expressed in an IPTG-dependent manner in *Corynebacterium glutamicum*.

This method has been employed, for example, in the patent WO 02266787 for regulated expression of the deaD gene by means of integration of the vector pXK99EdeaD into the genome of *Corynebacterium glutamicum*, and by Simic et al. (Applied and Environmental Microbiology 68: 3321-3327 (2002)) for regulated expression of the glyA gene by means of integration of the vector pK18mobglyA' into *Corynebacterium glutamicum*.

Another method for specifically reducing gene expression is the antisense technique which involves delivering into the target cells short oligodeoxynucleotides or vectors for synthesizing longer antisense RNA. There, the antisense RNA can bind to complementary sections of specific mRNAs and reduce their stability or block translatability. An example of this can be found by the skilled worker in Srivastava et al. (Applied Environmental Microbiology 2000 October; 66 (10): 4366-4371).

The rate of elongation is influenced by the codon usage. Gene expression may be attenuated by using codons for t-RNAs which are rare in the parent strain. This is described in detail in WO 2008049781 and in WO 2009133063. For example, replacing an ATG start codon with the less common codons GTG or TTG may impair translation, since the AUG codon is twice to three times as effective as the GUG and UUG codons, for example (Khudyakov et al., FEBS Letters 232(2): 369-71 (1988); Reddy et al., Proceedings of the National Academy of Sciences of the USA 82(17): 5656-60 (1985)).

It is likewise possible, in addition to the measures relating to the polynucleotide coding for a protein having L-ornithine export activity, to enhance individual biosynthesis genes.

To improve L-ornithine production, it is thus expedient, where appropriate, additionally to enhance the enzyme activity of one or more of the proteins selected from the group consisting of a) glutamate dehydrogenase (EC 1.4.1.3) encoded by the gdh gene,
b) glutamate N-acetyltransferase (EC 2.3.1.35 and EC 2.3.1.1) encoded by the argJ gene,
c) acetyl glutamate kinase (EC 2.7.2.8) encoded by the argB gene,
d) N-acetyl-gamma-glutamyl-phosphate reductase (EC 1.2.1.38) encoded by the argC gene,
e) acetylornithine aminotransferase (EC 2.6.1.11), encoded by the argD gene,
f) glucose-specific component EIIB (PtsG) (EC 2.7.1.69) of the glucose uptake system, encoded by the ptsG gene,
g) sucrose-specific component EIIB (PtsS) (EC 2.7.1.69) of the sucrose uptake system, encoded by the ptsS gene,
h) glucose-6-phosphate 1-dehydrogenase (EC 1.1.1.49) encoded by the zwf gene,
i) glucose-6-phosphate isomerase (EC 5.3.1.9) encoded by the pgi gene,
j) phosphofructokinase (EC 2.7.1.11) encoded by the pfkA gene,
k) fructose-bisphosphate aldolase (EC 4.1.2.13) encoded by the fda gene,
l) glyceraldehyde-3-phosphate dehydrogenase (EC 1.2.1.59) encoded by the gap gene,
m) phosphoglycerate kinase (EC 2.7.2.3) encoded by the pgk gene,
n) pyruvate kinase (EC 2.7.1.40) encoded by the pyk gene,
o) E1 subunit of pyruvate dehydrogenase (EC 1.2.4.1), encoded by the aceE gene,
p) phosphoenolpyruvate carboxylase (EC 4.1.1.31) encoded by the ppc gene,
q) pyruvate carboxylase (EC 6.4.1.1), encoded by the pyc gene,
r) aconitase (EC 4.2.1.3) encoded by the acn gene, and
s) isocitrate dehydrogenase (EC 1.1.1.42) encoded by the icd gene.

The term enhancement comprises the overexpression measures and the use of variants which have increased catalytic activity compared to the protein of the wild type.

Particular preference is given to enhancing one or more of the enzymes selected from the group consisting of glutamate dehydrogenase, glutamate N-acetyltransferase and acetylglutamate kinase.

The additional measures of attenuation listed may be combined with the additional measures of enhancement.

Instructions for the handling of DNA, digestion and ligation of DNA, transformation and selection of transformants can be found, inter alia, in the known manual by Sambrook et al. "Molecular Cloning: A Laboratory Manual, Second Edition (Cold Spring Harbor Laboratory Press, 1989).

The extent of expression or overexpression can be determined by measuring the amount or concentration of mRNA transcribed from the gene, by determining the amount or concentration of the polypeptide and by determining the level of enzyme activity.

The amount of mRNA may be determined, inter alia, by using the methods of "Northern blotting" and quantitative RT-PCR.

In quantitative RT-PCR, the polymerase chain reaction is preceded by a reverse transcription. It is possible to use for this purpose the LightCycler™ system from Roche Diagnostics (Boehringer Mannheim GmbH, Roche Molecular Biochemicals, Mannheim, Germany), as described in Jungwirth et al. (FEMS Microbiology Letters 281, 190-197 (2008)), for example. The concentration of the protein may be determined by 1- and 2-dimensional protein gel fractionation and subsequent optical identification of the protein concentration in the gel using appropriate evaluation software. A common method of preparing the protein gels for coryneform bacteria and of identifying the proteins is the procedure described by Hermann et al. (Electrophoresis, 22: 1712-23 (2001)). The protein concentration may likewise be determined by Western-blot hybridization using an antibody which is specific for the protein to be detected (Sambrook et al., Molecular cloning: a laboratory manual, $2^{nd}$ Ed. Cold Spring Harbor Laboratory Press, Cold Spring Harbor, N.Y., 1989) and subsequent optical evaluation using appropriate concentration determination software (Lohaus and Meyer (1998) Biospektrum 5: 32-39; Lottspeich, Angewandte Chemie 321: 2630-2647 (1999)).

The bacteria produced may be cultured continuously—as described, for example, in WO 05/021772—or discontinuously in a batch process (batch cultivation) or in a fed-batch or repeated fed-batch process (described in U.S. Pat. No. 6,562, 601 for example) for the purpose of producing L-ornithine. A summary of a general nature about known cultivation methods is available in the text book by Chmiel (Bioprozesstechnik [Bioprocess Technology] 1. Einführung in die Bioverfahrenstechnik [Introduction to Bioprocess Engineering] (Gustav Fischer Verlag, Stuttgart, 1991)), or in the text book by Storhas (Bioreaktoren and periphere Einrichtungen [Bioreactors and Peripheral Equipment] (Vieweg Verlag, Brunswick/Wiesbaden, Germany 1994)).

The culture medium or fermentation medium to be used must in a suitable manner satisfy the demands of the particular strains. The "Manual of Methods for General Bacteriology" of the American Society for Bacteriology (Washington D.C., USA, 1981) contains descriptions of culture media for various microorganisms. The terms growth medium, culture medium and fermentation medium or medium are interchangeable.

It is possible to use, as carbon source, sugars and carbohydrates such as, for example, glucose, sucrose, lactose, fructose, maltose, molasses, sucrose-containing solutions from sugar-beet or sugar-cane processing, starch, starch hydrolysate and cellulose, oils and fats such as, for example, soya oil, sunflower oil, groundnut oil and coconut fat, fatty acids such as, for example, palmitic acid, stearic acid and linoleic acid, alcohols such as, for example, glycerol, methanol and ethanol, and organic acids such as, for example, acetic acid or lactic acid.

With sugars, preference is given to glucose, fructose, sucrose, mixtures of glucose and fructose, and mixtures of glucose, fructose and sucrose. Where appropriate, particular preference is given to sucrose.

With alcohols, preference is given to glycerol.

It is possible to use, as nitrogen source, organic nitrogen-containing compounds such as peptones, yeast extract, meat extract, malt extract, corn steep liquor, soybean flour and urea, or inorganic compounds such as ammonium sulphate, ammonium chloride, ammonium phosphate, ammonium carbonate and ammonium nitrate. The nitrogen sources may be used individually or by way of a mixture.

It is possible to use, as phosphorus source, phosphoric acid, potassium dihydrogen phosphate or dipotassium hydrogen phosphate or the corresponding sodium-containing salts.

The culture medium must furthermore comprise salts, for example in the form of chlorides or sulphates of metals such as, for example, sodium, potassium, magnesium, calcium and iron, such as magnesium sulphate or iron sulphate for example, which are necessary for growth. Finally, essential growth factors such as amino acids, for example homoserine and vitamins, for example thiamine, biotin or pantothenic acid, may be employed in addition to the above-mentioned substances.

The starting materials mentioned may be added to the culture in the form of a single batch or be fed in in a suitable manner during cultivation.

The pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of plasmids, it is possible to add to the medium suitable selective substances such as, for example, antibiotics. The fermentation is preferably carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch processes, preference is given to continuing culturing until an amount of the desired L-ornithine sufficient for being recovered has formed. This aim is normally achieved within 10 hours to 160 hours. With continuous processes, longer culturing times are possible. The bacterial activity results in a concentration or an increase in the concentration (accumulation) of L-ornithine in the fermentation medium.

Example of suitable fermentation media can be found inter alia in the patents JP 43010996 B4 (for *B. subtilis*), U.S. Pat. No. 3,668,072 A (for *E. coli*) and JP 57041912 B (for *B. flavum*).

Where appropriate, the volume of the fermentation medium in a process according to the invention is ≥0.5 l, ≥1 l, ≥5 l, ≥10 l, ≥50 l, ≥100 l, ≥500 l, ≥1000 l, preferably ≥1 l, particularly preferably ≥10 l, very particularly preferably 100 l and most preferably ≥1000 l.

To determine the concentration at one or more time point(s) in the course of the fermentation, L-ornithine may be analysed by separating the L-amino acids by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthaldialdehyde rather than ninhydrin for post-column derivatization. An overview article on ion exchange chromatography can be found in Pickering (LC.GC (Magazine of Chromatographic Science) 7(6), 484-487 (1989)).

It is likewise possible to carry out a pre-column derivatization, for example using ortho-phthaldialdehyde or phenyl isothiocyanate, and to fractionate the resulting amino acid derivatives by reversed-phase chromatography (RP), preferably in the form of high-performance liquid chromatography (HPLC). A method of this type is described, for example, in Lindroth et al. (Analytical Chemistry 51: 1167-1174 (1979)). Detection is carried out photometrically (absorbance, fluorescence).

A review regarding amino acid analysis can be found inter alia in the text book "Bioanalytik" by Lottspeich and Zorbas (Spektrum Akademischer Verlag, Heidelberg, Germany 1998).

The performance of the processes or fermentation processes according to the invention, in respect of one or more of the parameters selected from the group consisting of L-ornithine concentration (L-ornithine formed per volume), L-ornithine yield (L-ornithine formed per carbon source consumed), L-ornithine formation (L-ornithine formed per volume and time), and specific L-ornithine formation (L-ornithine formed per dry cell matter or dry biomass and time, or L-ornithine formed per cellular protein and time), or else other process parameters and combinations thereof, is increased by at least 0.5%, at least 1%, at least 1.5% or at least 2%, based on processes or fermentation processes using bacteria which contain a non-overexpressed protein having L-ornithine export activity or which have not been subjected to an overexpression measure.

The fermentation measures result in a fermentation broth which contains the desired L-ornithine.

A product containing L-ornithine is then provided or produced or recovered in liquid or solid form.

A fermentation broth means a fermentation medium or growth medium in which a microorganism has been cultured for a certain time and at a certain temperature. The fermentation medium or the media employed during fermentation comprises/comprise all the substances or components which ensure production of said L-ornithine and typically propagation and viability.

When the fermentation is complete, the resulting fermentation broth accordingly comprises
a) the bacterial biomass (cell mass) produced due to propagation of the bacterial cells,
b) the L-ornithine formed in the course of the fermentation,
c) the organic by-products formed in the course of the fermentation, and
d) the constituents of the fermentation medium employed or of the starting materials, for example vitamins such as biotin or salts such as magnesium sulphate, which have not been consumed in the fermentation.

The organic by-products include substances which are produced by the bacteria employed in the fermentation in addition to the L-ornithine and are optionally eliminated. These also include sugars such as trehalose, for example.

The fermentation broth is removed from the culture vessel or fermentation tank, optionally collected, and used for providing an L-ornithine-containing product in liquid or solid form. The expression "recovering the L-ornithine-containing product" is also used for this. In the simplest case, the L-ornithine-containing fermentation broth itself, which has been removed from the fermentation tank, constitutes the recovered product.

One or more of the measures selected from the group consisting of
a) partial (>0% to <80%) to complete (100%) or virtually complete (≥80%, ≥90%, ≥95%, ≥96%, ≥97%, ≥98% or ≥99% to <100%) removal of water,
b) partial (>0% to <80%) to complete (100%) or virtually complete (≥80%, ≥90%, ≥95%, ≥96%, ≥97%, ≥98% or ≥99% to <100%) removal of the biomass which is optionally inactivated before removal,
c) partial (>0% to <80%) to complete (100%) or virtually complete (80%, ≥90%, ≥95%, ≥96%, ≥97%, ≥98%, ≥99%, ≥99.3% or ≥99.7% to <100%) removal of the organic by-products formed in the course of the fermentation, and
d) partial (>0%) to complete (100%) or virtually complete (≥80%, ≥90%, ≥95%, ≥96%, ≥97%, ≥98%, ≥99%, ≥99.3% or ≥99.7% to <100%) removal of the constituents of the fermentation medium employed or of the starting materials, which have not been consumed in the fermentation, from the fermentation broth achieves concentration or purification of the L-ornithine. Products having a desired L-ornithine content are isolated in this way.

The partial (>0% to <80%) to complete (100%) or virtually complete (≥80% to <100%) removal of water (measure a)) is also referred to as drying.

In one variant of the process, complete or virtually complete removal of water, of the biomass, of the organic by-products and of the unconsumed constituents of the fermentation medium employed results in pure (≥80% by weight or ≥90% by weight) or high-purity (≥95% by weight, ≥97% by weight or ≥99% by weight) L-ornithine product forms. An abundance of technical instructions for the measures according to a), b), c) or d) are available in the prior art.

In the case of the amino acid L-ornithine or its salts, essentially three different products have been described in the prior art.

One group describes L-ornithine HCL, from which L-ornithine is purified from the fermentation solution, after removal of the cells by means of an ion exchanger, and then crystallized through crystallization as L-ornithine monochloride and recrystallization as L-ornithine monochloride (U.S. Pat. No. 2,988,489). The L-ornithine HCL obtained in this case has a purity of more than >90%, preferably more than 95%, particularly preferably more than 98%, and very particularly preferably more than 99%.

A further process is described in the patent application EP 1995322. This involves applying the biomass-containing fermentation solution to the top of a weakly acidic ion exchanger with a particle diameter of >300 μm and purifying the L-ornithine by this step. The selection of an appropriate particle diameter prevents the biomass from blocking the resin. The efficiency of cell removal was 99%.

The purified L-ornithine may then be employed for preparing various L-ornithine salts such as, for example, mono- or di-L-ornithine α-ketoglutarate, L-ornithine L-aspartate, etc.

EP 0477 991, for example, describes a process for preparing L-ornithine L-aspartate. This involves adding to an aqueous solution of L-ornithine and L-aspartate a water-soluble solvent in order to arrive at a solution which is at least 90% saturated or over saturated. Said solution is heated under reflux until the formation of crystals has ended. A water-miscible solvent is then continued to be added under reflux until the salt crystals form. The crystals may be removed, for example, by centrifugation and are subsequently dried under vacuum. The product purity is typically above 98.5%.

JP 46003194 describes a process for preparing L-ornithine L-ketoglutarate. This involves, for example, converting ornithine HCL into the free base by means of adsorption to an acidic ion exchanger and elution with aqueous ammonia, adding α-ketoglutarate and evaporating the solution under vacuum until the product crystallizes.

The plasmid pEC7lysE has been deposited in the form of the strain *Escherichia coli* DH5alpha/pEC7lysE (DM2204) in accordance with the Budapest Treaty with the Deutsche Sammlung von Mikroorganismen and Zellkulturen (DSMZ, Brunswick, Germany) under accession number DSM 23239 on 15 Jan. 2010.

EXAMPLES

Example 1

Cloning and Sequencing of the lysE Gene from *Corynebacterium glutamicum* ATCC 13032

The lysE gene of strain ATCC13032 was cloned into the *E. coli/C. glutamicum* shuttle and expression vector pVWEx1 (Peters-Wendisch et al., J. Mol. Microbiol. Biotechnol. (2001) 3(2): 295-300).

Cloning was carried out in two steps. First, a polymerase chain reaction (PCR) amplified the gene from *Corynebacterium glutamicum* ATCC13032 by means of the following oligonucleotide primers derived from SEQ ID No. 1. Said oligonucleotides included additional restriction cleavage sites on their 5' end (underlined: EcoRV for lysE__1.p and AvrII or SspI for lysE__2.p).

(see SEQ ID No. 22)
lysE_1.p: 5'-[TC<u>GATATC</u>ATGGAAATCTTCATTACAGG]-3'

(see SEQ ID No. 23)
lysE_2.p: 5'-[TG<u>CCTAGGT</u>C<u>AATATT</u>TGGGCGAAGGCCACCG]-3'

The PCR reaction was carried out in the presence of 200 μM deoxynucleoside triphosphates (dATP, dCTP, dGTP, dTTP), 0.5 μM each of the corresponding oligonucleotide, 100 ng of *Corynebacterium glutamicum* ATCC13032 chromosomal DNA, ⅕ volume of 5 times reaction buffer HF and 0.02 U/μl Phusion®Hot Start DNA polymerase (Biozym Scientific GmbH, D-31840 Hess. Oldendorf) in a thermocycler (Mastercycler, Eppendorf AG, Hamburg) under the following conditions: 98° C. for 1 min; 30 cycles×(98° C., 20 s; 63° C., 20 s; 72° C., 40 s); 72° C. for 6 min.

The 761 bp lysE PCR fragment (see SEQ ID No. 3) was cloned into pVWEx1 as described below:

Preparation of the vector: 1 μg of pVWEx1 plasmid DNA was cleaved in the enzyme-specific buffer system containing 10 units of the enzyme PstI by incubation at 37° C. for 1 h. Immediately thereafter, the cleavage mix was treated with the Quick Blunting Kit (New England Biolabs GmbH, Frankfurt am Main) according to the manufacturer's instructions and then purified using the QiaExII purification kit (Qiagen AG, Hilden, Germany) according to the manufacturer's instructions. The vector pre-treated in this way was then cleaved with 10 units of XbaI in the enzyme-specific buffer system at 37° C. for 1 h and then purified again using the QiaExII purification kit.

Preparation of the insert: the lysE PCR fragment was cleaved with 10 units each of the enzymes AvrII and EcoRV and then purified using the QiaExII purification kit according to the manufacturer's instructions.

Ligation: vector and insert were mixed at a 1:5 molar ratio and ligated using T4 DNA ligase at 16° C. for 1 h. Chemical competent *E. coli* DH5alpha cells (Subcloning efficiency, Invitrogen GmbH, Karlsruhe, Germany) were transformed with 3 µl of the ligation mix.

Transformants were identified on the basis of their kanamycin resistance on LB-agar plates containing 50 µg/ml kanamycin sulphate. Plasmid DNA was isolated from 4 of said transformants, and the plasmids were assayed by restriction analysis for the presence of the 0.75 kb fragment as insert. The recombinant plasmid produced in this way was referred to as pVWEx1_lysE.

The nucleotide sequence of the 0.75 kb fragment in plasmid pVWEx1-lysE was determined by the dideoxy chain termination method according to Sanger et al. (Proceedings of the National Academy of Sciences of the United States of America (1977) 74: 5463-5467). To this end, the complete insert of the pVWEx1_lysE plasmid was sequenced with the aid of the oligonucleotide primers pVW_1.p (5'-TGA GCG GAT AAC AAT TTC ACA C-3') and pVW_2.p (5'-CGA CGG CCA GTG AAT TCG AG-3') at Eurofins MWG Operon GmbH (Ebersberg, Germany).

The nucleotide sequence obtained was analysed using the Clone Manager 9 Program and is depicted by way of SEQ ID No. 20.

Example 2

Construction of the Vector pK18mobsacB_DargFRGH for Deletion of the argFRGH Region in *Corynebacterium glutamicum*

To this end, firstly chromosomal DNA was isolated from *C. glutamicum* ATCC13032 by the method of Tauch et al. (1995, Plasmid 33: 168-179). The oligonucleotides listed below were selected on the basis of the sequence of the *C. glutamicum* argFRGH genes in order to prepare the argFRGH deletion construct. Said deletion construct was generated with the aid of the polymerase chain reaction (PCR), more specifically by the gene SOEing method (Gene Splicing by Overlap Extension, Horton, Molecular Biotechnology 3: 93-98 (1995)).

```
argFRGH_d1:
                                    (see SEQ ID No. 24)
5'-GGT GGT GCT AGC CCG GCG ATT TCT TTG CAC AT-3' argFRGH_d2:
                                    (see SEQ ID No. 25)
5'-AAT GCT TAT CGA CGT ACC CCC CTG TGG TTG TGA AGT
CAT A-3' argFRGH_d3:
                                    (see SEQ ID No. 26)
5'-GGG GTA CGT CGA TAA GCA TT-3' argFRGH_d4:
                                    (see SEQ ID No. 27)
5'-GGT GGT ATG CAT GGT GAT GGT TCC GAA TGT TG-3'
```

The oligonucleotide primers depicted were purchased from Eurofins MWG Operon GmbH (Ebersberg, Germany). The PCR reaction was carried out using the Phusion® Hot Start DNA polymerase (Biozym Scientific GmbH, D-31840 Hess, Oldendorf) in a thermocycler (Mastercycler, Eppendorf AG, Hamburg).

The argFRGH_d2 primer is composed of two regions. One part of the nucleotide sequence is complementary to the region from 1 bp upstream to 19 bp downstream of the start codon of the argF gene. The other part of the nucleotide sequence is complementary to the region from nucleotide 1419 of the argH gene to 5 nucleotides downstream of the argH gene.

With the aid of the polymerase chain reaction, the primers argFRGH_1 and argFRGH_2 enable a 543 bp DNA fragment and the primers argFRGH_3 and argFRGH_4 enable a 513 bp DNA fragment to be amplified. The amplicons were produced by PCR, assayed by electrophoresis in a 0.8% strength agarose gel, isolated from said agarose gel using the High Pure PCR Product Purification Kit (Product No. 1732676, Roche Diagnostics GmbH, Mannheim, Germany), and employed as template for another PCR reaction using the primers argFRGH_1 and argFRGH_4. In this way, the 1036 bp DargFRGH deletion derivative was generated (see also SEQ ID No. 21). It includes 477 bp of the 3' end of the argD gene, 19 bp of the 5' end of the argF gene, 15 bp of the 3' end of the argH gene, and 420 bp of the 5' end of the cg1589 reading frame. The product amplified in this way was assayed by electrophoresis in a 0.8% strength agarose gel.

The 1.04 kb DargFRGH PCR product (SEQ ID No. 21) was cleaved completely by the enzymes NdeI and NsiI. The fragment was subsequently purified using the PCR purification kit (Qiagen, Hilden, Germany). The DargFRGH deletion derivative pre-treated in this way was employed together with the mobilizible cloning vector pK18mobsacB (Schafer et al. (1994), Gene 14: 69-73) for ligation. Said cloning vector had previously been cleaved completely by the restriction endonucleases XbaI and PstI. This produced DNA ends compatible to the ends of the insert generated by NdeI and NsiI cleavage. The vector prepared in this way was mixed with the DargFRGH fragment at a 1:5 molar ratio and ligated using T4 DNA ligase (Amersham-Pharmacia, Freiburg, Germany) at 16° C. for 1 hour. Chemical competent *E. coli* DH5alpha cells (Subcloning efficiency, Invitrogen GmbH, Karlsruhe, Germany) were transformed with 3 µl of the ligation mix. Transformants were identified on the basis of their kanamycin resistance on LB-agar plates containing 50 µg/ml kanamycin sulphate. Plasmid DNA was isolated from 4 of said transformants (QIAprep Spin Miniprep Kit from Qiagen (Hilden)), and the plasmids were assayed by restriction analysis for the presence of the 1.04 kb fragment as insert. The recombinant plasmid produced in this way was referred to as pK18mobsacB_DargFRGH. The strain was referred to as *E. coli*_DH5alpha/pK18mobsacB_DargFRGH.

The nucleotide sequence of the 1.04 kb fragment (SEQ ID No. 21) in the pK18mobsacB_DargFRGH plasmid was determined by the dideoxy chain termination method according to Sanger et al. (Proceedings of the National Academy of Sciences of the United States of America (1977) 74: 5463-5467). To this end, the complete insert of the pK18mobsacB_DargFRGH plasmid was sequenced and thus assayed for correctness with the aid of the oligonucleotide primers M13 uni (−21) (5'-TGT AAA ACG ACG GCC AGT-3') and M13 rev (−49) (5'-GAG CGG ATA ACA ATT TCA CAC AGG-3') at Eurofins MWG Operon (Ebersberg, Germany).

Example 3

Preparation of the Strain *Corynebacterium glutamicum* ATCC 13032_DargFRGH

The vector mentioned in Example 2, pK18mobsacB_DargFRGH, was transferred by means of conjugation according to a protocol by Schäfer et al. (Journal of Microbiology 172: 1663-1666 (1990)) into the *Corynebacterium glutamicum* strain ATCC13032. For this purpose, the vector had previously been transformed into the *E. coli* strain S17-1 (Simon et al., Biotechnology 1: 784-791). The vector in S17-1 was assayed for identity similarly to detection in *E. coli* DH5alpha (see Example 2).

The vectors pK18mobsacB and pK18mobsacB_Darg FRGH cannot self-replicate in *C. glutamicum* ATCC13032 and remain in the cell only if they have integrated into the chromosome following a recombination event. Clones with integrated pK18mobsacB_Darg FRGH are selected by plating out the conjugation mix on LB agar (Sambrook et al., Molecular Cloning: A Laboratory Manual, $2^{nd}$ Ed., Cold Spring Harbor, N.Y., 1989) supplemented with 15 mg/l kanamycin and 50 mg/ml nalidixic acid. Established clones are struck out on LB-agar plates containing 25 mg/l kanamycin and incubated at 33° C. for 16 hours. Mutants in which the plasmid has been excised due to a second recombination event are selected by culturing the clones in LB liquid medium without selection for 20 hours, then striking them out on LB agar containing 10% sucrose, followed by incubation for 24 hours.

The pK18mobsacB_DargFRGH plasmid, like the pK18mobsacB starting plasmid, contains in addition to the kanamycin resistance gene a copy of the sacB gene coding for *Bacillus subtilis* levansucrase. Sucrose-inducible expression leads to the formation of levansucrase which catalyses the synthesis of the product levan which is toxic to *C. glutamicum*. Consequently, only those clones in which the integrated pK18mobsacB_DargFRGH has been excised again establish growth on LB agar containing sucrose. Excision may comprise excision of the plasmid together with either the complete chromosomal copy of argFRGH or the incomplete copy having the internal argFRGH deletion.

Approximately 40 to 50 colonies were tested for the phenotype "growth in the presence of sucrose" and "no growth in the presence of kanamycin". In order to prove that the deleted argFRGH allele has remained in the chromosome, approximately 20 colonies having the phenotype "growth in the presence of sucrose" and "no growth in the presence of kanamycin" were studied by the standard PCR method of Innis et al. (PCR Protocols. A Guide to Methods and Applications, 1990, Academic Press) with the aid of the polymerase chain reaction. This involved amplifying from the chromosomal DNA of the colonies a DNA fragment which carries the regions surrounding the deleted argFRGH region. The following primer oligonucleotides were selected for the PCR.

```
argFRGH_d1 (SEQ ID No. 24):
5'-GGT GGT GCT AGC CCG GCG ATT TCT TTG CAC AT-3' argFRGH_d4 (SEQ ID No. 27):
5'-GGT GGT ATG CAT GGT GAT GGT TCC GAA TGT TG-3'
```

In control clones containing the complete argFRGH locus, the primers enable an approx. 5.35 kb DNA fragment to be amplified. In clones having a deleted argFRGH locus, DNA fragments of approx. 1.04 kb in size are amplified.

The amplified DNA fragments were identified by means of electrophoresis in a 0.8% strength agarose gel. By this the strain was shown to carry a deleted argFRGH allele on the chromosome. The strain was referred to as *Corynebacterium glutamicum* Delta_argFRGH.

Example 4

Expression of the lysE Gene in *Corynebacterium glutamicum* ATCC 13032 Delta_argFRGH The plasmid pVWEx1_LysE and the empty plasmid pVWEx1 were introduced into the L-ornithine-forming strain ATCC 13032_Delta_argFGH by means of electroporation (Haynes et al., FEMS Microbiology Letters (1989) 61: 329-334). Transformants were identified on the basis of their kanamycin resistance on Caso agar plates containing 25 μg/ml kanamycin. 5 single clones were subsequently tested for correctness of the transformed plasmid. For this purpose, plasmid DNA was isolated (Plasmid Isolation Kit, Qiagen), and this DNA was assayed by restriction analysis for the correct cleavage pattern. In this way, the *C. glutamicum* strains ATCC 13032_Delta_argFRGH/pVWEx1_lysE and ATCC 13032_Delta_argFRGH/pVWEx1 were produced.

Example 5

Preparation of L-Ornithine Using *Corynebacterium glutamicum*

In order to study their ability to produce L-ornithine, in each case three clones of strain ATCC 13032_Delta_argFRGH/pVWEx1_lysE and three clones of strain ATCC 13032_Delta_argFRGH/pVWEx1 were pre-cultured in each case in 10 ml of test medium at 33° C. for 16 h. For the production assay, in each case 10 ml of test medium were inoculated with the pre-culture obtained in such a way that the $OD_{600}$ (optical density at 600 nm) at the start was 0.1. Each clone was tested in three shaker flasks so that each strain is represented at the respective harvesting time by nine shaker flasks in total.

The test medium was identical to the CgXII medium described in Keilhauer et al. (Journal of Bacteriology (1993) 175: 5593-5603) but additionally contained 7.5 g/l yeast extract (Difco), 25 μg/ml kanamycin, 1 mM IPTG (isopropyl beta-D-thiogalactopyranoside) and 40 g/l sucrose instead of glucose. For reasons of simplicity, the composition of the test medium is summarized in Table 2 below.

TABLE 2

| Component | Content per 1 |
|---|---|
| $(NH_4)_2SO_4$ | 20 g |
| Urea | 5 g |
| $KH_2PO_4$ | 1 g |
| $K_2HPO_4$ | 1 g |
| $MgSO_4 \times 7H_2O$ | 0.25 g |
| 3-Morpholinopropanesulphonic acid (MOPS) | 42 g |
| $CaCl_2$ | 0.01 g |
| $FeSO_4 \times 7H_2O$ | 0.01 g |
| $MnSO_4 \times H_2O$ | 0.01 g |
| $ZnSO_4 \times 7H_2O$ | 0.001 g |
| $CuSO_4$ | 0.0002 g |
| $NiCl_2 \times 6H_2O$ | 0.00002 g |
| Biotin | 0.0002 g |
| Protocatechuic acid | 0.03 g |
| Sucrose | 40 g |
| Yeast extract | 7.5 g |
| Ph (with NaOH) | 7 |

The cultivation was carried out in 100 ml shaker flasks at 33° C. and 200 rpm. The deflection of the shaker was 5 cm. Three cultures of a clone were harvested after 24 and 48 hours. To this end, samples were taken from the cultures and the optical density, the sucrose content and the L-ornithine-content were determined. To determine the sucrose and L-ornithine contents the cells were removed by brief centrifugation (table-top centrifuge type 5415D (Eppendorf) at 13 000 rpm, 10 min, room temperature).

The optical density was determined at a wavelength of 660 nm, using a GENios microtitre plate photometer (Tecan, Reading, UK). The samples were diluted 1:100 with demineralized water prior to the measurement.

Sucrose was determined using a test system (Cat. No. 10 716 251 035) from R-Biopharm AG (Darmstadt, Germany). This involves inversion of sucrose and the glucose formed being detected using a coupled enzyme assay (hexokinase/glucose-6-phosphate dehydrogenase) via NADH formation.

Quantitative determination of the extracellular amino acid concentration from the culture supernatant was carried out by means of reverse-phase HPLC (Lindroth et al., Analytical Chemistry (1979) 51: 1167-1174), using an HP1100 series HPLC instrument (Hewlett-Packard, Waldbronn, Germany) with connected fluorescence detector (G1321A); system control and data evaluation were carried out using a HP Chem-Station (Hewlett-Packard). 1 µL of the amino acid solution to be analysed was mixed in an automatic pre-column derivatization with 20 µl of ready-to-use ortho-phthaladehyde/2-mercaptoethanol reagent (Pierce Europe BV, Oud-Beijerland, Netherlands). The resulting fluorescent, thio-substituted isoindoles (Jones et al., Journal of Chromatography (1983) 266: 471-482) were fractionated on a pre-column (40×4 mm Hypersil ODS 5) and main-column combination (Hypersil ODS 5, both columns from CS-Chromatographie Service GmbH, Langerwehe, Germany) using a gradient program with an increasingly non-polar phase (methanol). The polar eluent was sodium acetate (0.1 M; pH 7.2); the flow rate was 0.8 mL per minute. The fluorescence of the derivatized amino acids was detected at an excitation wavelength of 230 nm and an emission wavelength of 450 nm. The L-ornithine and/or L-ornithine hydrochloride concentrations were calculated by way of comparison with an external standard and L-asparagine as additional internal standard.

The molecular weight of L-ornithine hydrochloride is 168.6 g×mol$^{-1}$ and that of L-ornithine is 132.1 g×mol$^{-1}$.

The yield was calculated by dividing the amount of L-ornithine formed (measured as L-ornithine hydrochloride) by the amount of sucrose consumed.

The results are listed in Table 3.

TABLE 3

L-ornithine formation after 24 hours (Table 3A) and 48 hours (Table 3B) of incubation.

Table 3A:

| Time | 24 hours | | |
|---|---|---|---|
| Strain | Orn-HCl g/l | Yield g/g | OD |
| */pVWEx1 | 9.83 ± 0.10 | 0.39 ± 0.01 | 10.78 ± 0.30 |
| */pVWEx1_lysE | 13.03 ± 0.16 | 0.44 ± 0.01 | 10.40 ± 0.41 |

TABLE 3-continued

L-ornithine formation after 24 hours (Table 3A) and 48 hours (Table 3B) of incubation.

Table 3B:

| Time | 48 hours | | |
|---|---|---|---|
| Strain | Orn-HCl g/l | Yield g/g | OD |
| */pVWEx1 | 15.50 ± 0.74 | 0.36 ± 0.01 | 11.69 ± 1.40 |
| */pVWEx1_lysE | 18.48 ± 0.51 | 0.42 ± 0.01 | 9.18 ± 0.48 |

Abbreviations:
*ATCC 13032_Delta_argFRGH; Orn-HCl: L-ornithine hydrochloride.

Example 6

Sequencing and Deposition of Plasmid pEC7lysE

Plasmid pEC7lysE was made available in the form of an aqueous solution by Dr. Lothar Eggeling (Forschungszentrum Jülich GmbH, D-52425 Jülich), the corresponding author of the publication Bellmann et al. (Microbiology (2001) 147, 1765-1774).

An aliquot of the DNA solution obtained was employed for transforming competent *Escherichia coli* cells of the DH5alpha strain (subcloning efficiency, Genotype: F-Φ80lacZΔM15 Δ (lacZYA-argF) U169 recA1 endA1 hsdR17 (rK−, mk+) phoA supE44 λ-thi-1 gyrA96 relA1) from Invitrogen GmbH (Paisley, UK) according to the manufacturer's instructions. The transformants were selected on Luria-Bertani agar supplemented with 50 µg/ml kanamycin.

One transformant referred to as *Escherichia coli* DH5alpha/pEC7lysE(DM2204) was deposited according to the Budapest Treaty with the Deutsche Sammlung von Mikroorganismen and Zellkulturen GmbH (Brunswick, Germany) under the deposition number DSM 23239 on 15 Jan. 2010.

The pEC7lysE plasmid from the DSM 23239 strain was completely sequenced by custom DNA sequencing (Walking Service) at Eurofins MWG Operon GmbH (Martinsried, Germany). The sequence of pEC7lysE is listed as SEQ ID No. 29.

INCORPORATION BY REFERENCE

Each document, patent, patent application or patent publication cited by or referred to in this disclosure is incorporated by reference in its entirety, especially with respect to the specific related subject matter surrounding the citation of the reference in the text. However, no admission is made that any such reference constitutes background art and the right to challenge the accuracy and pertinency of the cited documents is reserved.

The invention claimed is:

1. A process for preparing L-ornithine, comprising:
   a) cultivating in a medium an L-ornithine excreting bacterium selected from the group consisting of *Corynebacterium, Bacillus, Streptomyces, Arthrobacter* and the Enterobacteriaceae which overexpresses a polynucleotide coding for a polypeptide which has the activity of an L-ornithine exporter and whose amino acid sequence is identical to the amino acid sequence of SEQ ID No. 2 or comprises SEQ ID NO: 2 with a maximum of 25 deletions, insertions, substitutions or N-terminal and/or C-terminal additions of amino acids overall thus producing a fermentation broth, and
   b) recovering L-ornithine from the fermentation broth,
   wherein plasmid pEC7lysE, deposited as DSM23239, is excluded for overexpression.

2. The process according to claim 1, wherein the encoded polypeptide comprises the amino acid sequence of SEQ ID No. 2.

3. The process according to claim 1, wherein said bacterium is *Corynebacterium glutamicum*, and wherein overexpression increases the level of L-ornithine export activity by at least 10%, compared to the bacteria deposited as ATCC13032, ATCC14067 or ATCC13869.

4. The process according to claim 1, wherein overexpression is achieved by one or more of the measures selected from the group consisting of
   a) increasing the copy number,
   b) using a strong promoter, and
   c) mutating the promoter, and
   d) overexpressing an activator protein.

5. The process according to claim 1, wherein the bacterium is a *Corynebacterium*.

6. The process according to claim 1, wherein the bacterium is *Corynebacterium glutamicum*.

7. The process according to claim 1, wherein additionally one or more of the genes selected from the group consisting of
   a) odhA gene coding for the E1 subunit of alpha-ketoglutarate dehydrogenase (EC 1.2.4.2),
   b) sucA gene coding for dihydrolipoamide succinyl transferase (EC 2.3.1.61),
   c) dapA gene coding for a dihydrodipicolinate synthase (DapA, EC 4.2.1.52),
   d) dapB gene coding for a dihydrodipicolinate synthase (DapB, EC 1.3.1.26),
   e) ddh gene coding for a meso-diaminopimelate dehydrogenase (Ddh, EC 1.4.1.16),
   f) lysA gene coding for a diaminopimelate decarboxylase (LysA, EC 4.1.1.20),
   g) argR gene coding for a/the repressor (ArgR) of L-arginine biosynthesis,
   h) argF gene coding for an ornithine carbamoyl transferase (ArgF, EC 2.1.3.3),
   i) argG gene coding for an argininosuccinate synthase (ArgG, EC 6.3.4.5),
   j) argH gene coding for an argininosuccinate lyase (ASAL) (ArgH, EC 4.3.2.1),
   k) lysC gene coding for an aspartate kinase (LysC, EC 2.7.2.4), and
   l) asd gene coding for an aspartate semialdehyde dehydrogenase (Asd, EC 1.2.1.11),
   is/are attenuated.

8. The process according to claim 1, wherein additionally one or more of the genes selected from the group consisting of
   a) glutamate dehydrogenase (EC 1.4.1.3) encoded by the gdh gene,
   b) glutamate N-acetyltransferase (EC 2.3.1.35 and EC 2.3.1.1) encoded by the argJ gene,
   c) acetylglutamatekinase (EC 2.7.2.8) encoded by the argB gene,
   d) N-acetyl-gamma-glutamyl-phosphate reductase (EC 1.2.1.38) encoded by the argC gene,
   e) acetylornithine aminotransferase (EC 2.6.1.11), encoded by the argD gene,
   f) glucose-specific component EIIB (PtsG) (EC 2.7.1.69) of the glucose uptake system, encoded by the ptsG gene,
   g) sucrose-specific component EIIB (PtsS) (EC 2.7.1.69) of the sucrose uptake system, encoded by the ptsS gene,
   h) glucose-6-phosphate 1-dehydrogenase (EC 1.1.1.49) encoded by the zwf gene,
   i) glucose-6-phosphate isomerase (EC 5.3.1.9) encoded by the pgi gene,
   j) phosphofructokinase (EC 2.7.1.11) encoded by the pfkA gene,
   k) fructose-bisphosphate aldolase (EC 4.1.2.13) encoded by the fda gene,
   l) glyceraldehyde-3-phosphate dehydrogenase (EC 1.2.1.59) encoded by the gap gene,
   m) phosphoglycerate kinase (EC 2.7.2.3) encoded by the pgk gene,
   n) pyruvate kinase (EC 2.7.1.40) encoded by the pyk gene,
   o) E1 subunit of pyruvate dehydrogenase (EC 1.2.4.1), encoded by the aceE gene,
   p) phosphoenolpyruvate carboxylase (EC 4.1.1.31) encoded by the ppc gene,
   q) pyruvate carboxylase (EC 6.4.1.1), encoded by the pyc gene,
   r) aconitase (EC 4.2.1.3) encoded by the acn gene, and
   s) isocitrate dehydrogenase (EC 1.1.1.42) encoded by the icd gene,
   is/are enhanced.

9. The process according to claim 1, which is a process selected from the group consisting of batch process, fed-batch process, repetitive fed-batch process, and continuous process.

10. The process according to claim 1, wherein L-ornithine or a liquid or solid L-ornithine-containing product is recovered from the L-ornithine-containing fermentation broth.

11. The process according to claim 1, wherein overexpression is achieved by increasing the copy number.

12. The process according to claim 1, wherein overexpression is achieved by using a strong promoter.

13. The process according to claim 1, wherein overexpression is achieved by mutating the promoter.

14. The process according to claim 1, wherein overexpression is achieved by overexpressing an activator protein.

* * * * *